US009434898B2

(12) United States Patent
Raney et al.

(10) Patent No.: US 9,434,898 B2
(45) Date of Patent: Sep. 6, 2016

(54) ALGAL LIPID COMPOSITIONS AND METHODS OF PREPARING AND UTILIZING THE SAME

(75) Inventors: Kyle A. Raney, Winchester, KY (US); Rebecca A. Timmons, Lexington, KY (US)

(73) Assignee: Alltech, Inc., Nicholasville, KY (US)

( * ) Notice: Subject to any disclaimer, the term of this patent is extended or adjusted under 35 U.S.C. 154(b) by 0 days.

(21) Appl. No.: 13/548,871

(22) Filed: Jul. 13, 2012

(65) Prior Publication Data

US 2013/0017594 A1    Jan. 17, 2013

Related U.S. Application Data

(60) Provisional application No. 61/507,390, filed on Jul. 13, 2011.

(51) Int. Cl.
| | |
|---|---|
| C12N 1/12 | (2006.01) |
| C10L 1/02 | (2006.01) |
| C11B 1/00 | (2006.01) |
| C12P 7/64 | (2006.01) |

(52) U.S. Cl.
CPC ............... *C10L 1/026* (2013.01); *C11B 1/00* (2013.01); *C12N 1/12* (2013.01); *C12P 7/64* (2013.01); *C12P 7/6463* (2013.01); *C10L 2200/0476* (2013.01); *C10L 2200/0484* (2013.01); *Y02E 50/13* (2013.01)

(58) Field of Classification Search
None
See application file for complete search history.

(56) References Cited

U.S. PATENT DOCUMENTS

| | | | |
|---|---|---|---|
| 3,891,504 A * | 6/1975 | Schocher et al. ............... 435/67 |
| 5,130,242 A * | 7/1992 | Barclay .......................... 435/134 |
| 5,340,594 A | 8/1994 | Barclay |
| 5,340,742 A | 8/1994 | Barclay |
| 5,518,918 A | 5/1996 | Barclay |
| 5,539,133 A * | 7/1996 | Kohn et al. ...................... 554/20 |
| 5,656,319 A | 8/1997 | Barclay |
| 5,688,500 A | 11/1997 | Barclay |
| 5,698,244 A | 12/1997 | Barclay |
| 5,908,622 A | 6/1999 | Barclay |
| 5,985,348 A | 11/1999 | Barclay |
| 6,103,225 A | 8/2000 | Barclay |
| 6,177,108 B1 | 1/2001 | Barclay |
| 6,410,281 B1 | 6/2002 | Barclay |
| 6,451,567 B1 | 9/2002 | Barclay |
| 6,566,123 B1 | 5/2003 | Barclay |
| 6,582,941 B1 * | 6/2003 | Yokochi et al. ............... 435/134 |
| 6,977,167 B2 | 12/2005 | Barclay |
| 7,005,280 B2 | 2/2006 | Barclay |
| 7,011,962 B2 | 3/2006 | Barclay |
| 7,022,512 B2 | 4/2006 | Barclay |
| 7,033,584 B2 | 4/2006 | Barclay |
| 7,381,558 B2 | 6/2008 | Barclay |
| 8,129,172 B2 | 3/2012 | Barclay |
| 8,288,135 B2 | 10/2012 | Barclay |
| 2001/0000151 A1 | 4/2001 | Barclay |
| 2003/0100097 A1 | 5/2003 | Barclay |
| 2003/0138477 A1 | 7/2003 | Barclay |
| 2004/0203121 A1 | 10/2004 | Barclay |
| 2004/0219648 A1 | 11/2004 | Barclay |
| 2006/0094089 A1 | 5/2006 | Barclay |
| 2006/0160203 A1 | 7/2006 | Barclay |
| 2006/0177920 A1 | 8/2006 | Barclay |
| 2006/0188969 A1 | 8/2006 | Barclay |
| 2007/0082384 A1 | 4/2007 | Barclay |
| 2007/0099280 A1 | 5/2007 | Barclay |
| 2007/0202126 A1 * | 8/2007 | Joerger et al. ........... 424/195.17 |
| 2008/0166780 A1 | 7/2008 | Barclay |
| 2008/0175953 A1 | 7/2008 | Barclay |
| 2008/0178739 A1 * | 7/2008 | Lewnard et al. ............... 95/186 |
| 2008/0199923 A1 | 8/2008 | Barclay |
| 2009/0209014 A1 | 8/2009 | Chi et al. |
| 2010/0233761 A1 * | 9/2010 | Czartoski et al. ........... 435/71.1 |

FOREIGN PATENT DOCUMENTS

| | | | |
|---|---|---|---|
| EP | 1251744 B1 | 10/2007 | |
| WO | 01/54510 | 8/2001 | |
| WO | WO 01/54510 | * 8/2001 | ............... A23B 7/10 |
| WO | 2006/107736 | 10/2006 | |
| WO | 2011/035042 | 3/2011 | |

OTHER PUBLICATIONS

Takagi et al., Appl. Microbiol. Biotechnol., 54:112-117 (2000).*
Yokochi et al., Appl. Microbiol. Biotechnol., 49:72-76 (1998).*
Yaguchi et al., J. Am. Oil. Chem. Soc. 74(11):1431-1434 (1997).*
Johnson et al., Energy Fuels, 23:5179-5183 (2009).*
Spolaore et al., J. Biosci. Bioeng., 101(2):87-96 (2006).*
Takagi et al., J. Biosci. Bioeng., 101(3):223-226 (2006).*
Raja et al., Seaweed Res. Utiln., 1-2:127-146 (2004).*
Ethier et al., Biores. Technol., 102:88-93 (2011).*
Tyson, K. S., Bozell, J., Wallace, R., Petersen, E., & Moens, L (2004). Biomass oil analysis: research needs and recommendations (No. NREL/TP-510-34796). National Renewable Energy Lab Golden Co.
Kusdiana, D., & Saka, S. (2004). Effects of water on biodiesel fuel production by supercritical methanol treatment. Bioresource technology, 91(3), 289-295.
Kusdiana, D., & Saka, S. (2001). Kinetics of transesterification in rapeseed oil to biodiesel fuel as treated in supercritical methanol. Fuel, 80(5), 693-698.
Saka, S., & Kusdiana, D. (2001). Biodiesel fuel from rapeseed oil as prepared in supercritical methanol. Fuel, 80(2), 225-231.
Stone, K. M., Roche, F. W., & Thornhill, N. F. (1992). Dry weight measurement of microbial biomass and measurement variability analysis. Biotechnology techniques, 6(3), 207-212.

(Continued)

*Primary Examiner* — Thomas J Visone
(74) *Attorney, Agent, or Firm* — Valerie L. Calloway; Kilyk & Bowersox, P.L.L.C.

(57) ABSTRACT

This invention relates to compositions comprising high lipid content algae and methods of making and utilizing the same. In particular, the invention relates to high lipid content algae biomass and algal lipid materials derived from the same, methods of making the same, as well as to biofuels (e.g., biodiesel) and dietary compositions (e.g., animal feeds) comprising or made from the same. Compositions and methods of the invention find use in a variety of applications including biofuel, dietary (e.g., human and animal nutrition), therapeutic as well as research applications.

23 Claims, 21 Drawing Sheets

(56) References Cited

OTHER PUBLICATIONS

Ferrell and Sarisky-Reed, National Algal Biofuels Technology Roadmap, U.S. Department of Energy, Published May 2010.
International Search Report for International Application No. PCT/US12/46696, dated Jan. 7, 2013.
Written Opinion of the International Searching Authority for International Application No. PCT/US12/46696, dated Jan. 7, 2013.
Supplemental Partial European Search Report issued in corresponding European Application No. 12810921, dated Feb. 10, 2015 (10 pages).
Extended European Search Report issued in corresponding European Application No. 12810921.2, dated Jun. 12, 2015 (15 pages).
Examination Report issued in corresponding New Zealand Patent Application No. 618123, dated Oct. 7, 2014 (2 pages).
Office Action issued in corresponding Ukrainian Patent Application No. a201315230, dated May 21, 2015, with English-language translation (12 pages).
Liang, Y., et al., "Use of sweet sorghum juice for lipid production by Schizochytrium limacinum SR21," Bioresource Technology, vol. 101, No. 10, Jan. 15, 2010, pp. 3623-3627.
Rosa, S. M., et al., "Improvement of a two-stage fermentation process for docosahexaenoic acid production by Aurantiochytrium limacinum SR21 applying statistical experimental designs and data analysis," Bioresource Technology, vol. 101, No. 7, Elsevier BV, GB, Dec. 16, 2009, pp. 2367-2374.
Zhu, L, et al., "Changes of lipid content and fatty acid composition of Schizochytrium limacinum in response to different temperatures and salinities," Process Biochemistry, vol. 42, No. 2, Elsevier, NL, Aug. 18, 2006, pp. 210-214.
Tran, H., et al., "Statistical Optimization of Culture Media for Growth and Lipid Production of Botryococcus braunii LB572," Biotechnology and Bioprocess Engineering, Korean Society for Biotechnology and Bioengineering, vol. 15, No. 2, Seoul, KR, May 9, 2010, pp. 277-284.
Li, Y., et al., "Comparison of growth and lipid content in three Botryococcus braunii strains," Journal of Applied Phycology, vol. 17, No. 6, Kluwer Academic Publishers, DO, Jan. 7, 2006, pp. 551-556.
Deng, X, et al., "Microalgae: A promising feedstock for biodiesel," African Journal of Microbiology Research, vol. 3, No. 13, Academic Journals, NG, Dec. 31, 2009, pp. 1008-1014.
Brennan, L., et al., "Biofuels from microalgae-A review of technologies for production, processing, and extractions of biofuels and co-products," Renewable and Sustainable Energy Reviews, vol. 14, No. 2, Elseviers Science, New York, NY, Oct. 29, 2009, pp. 557-577.
Su, C., et al., "Factors affecting lipid accumulation by Nannochloropsis oculata in a two-stage cultivation process," Journal of Applied Phycology, vol. 23, No. 5, Kluwer Academic Publishers, DO, Oct. 8, 2010, pp. 903-908.
Yeh, K., et al., "Nitrogen starvation strategies and photobioreactor design for enhancing lipid production of a newly isolated microalga Chlorella vulgaris ESP-31: Implications for biofuels," Biotechnology Journal, vol. 6, No. 11, Mar. 7, 2011, pp. 1358-1366.
Bassegio, G. (1974) "The composition of sea water and its concentrates", In: Coogan AH (ed.) 4th International Symposium on Salt, Houston, Texas, Apr. 8-12, 1973, vol. 2, pp. 351-358. Cleveland, OH: Northern Ohio Geological Society.
"Sea salts", Sigma-Aldrich, Product Specification for Product No. S9883, retrieved from Internet: http://www.sigmaaldrich.com/Graphics/COfAInfo/SigmaSAPQM/SPEC/S9/S9883/S9883-BULK_SIGMA_.pdf, retrieved Feb. 1, 2016, 2 pages.

* cited by examiner

| # 2011 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 8 | 20110609 | 313486 | F2-2-11 | Seed | 120000 | 123,600 | 53.71 | 55.32 | 70.81 |

(SL-F2-2-11) was inoculated on 5-31-11 from (G1A at log hour 73). This run was batched to 110,000 liters with media based on 120,000 liters. 1100 liters Fed batch media was added over a 38 hour period between log hours 24-62. 53,372 lbs of glucose was added during this run. The harvest was started on 06-03-11 at log hour 73. This run was clean and spray dried.

F2-3-11

| # 2011 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 10 | 20110705 | 314418 | F2-3-11 | Seed | 120,000 | 125,300 | 57.40 | 59.94 | 72.86 |

(SL-F2-3-11) was inoculated on 6-23-11 from (G1A at log hour 72). This run was batched to 110,000 liters with media based on 120,000 liters. 1100 liters Fed batch media was added over a 34 hour period between log hours 24 and 58. 64,693 lbs of glucose was added during this run. The harvest was started on 06-27-11 at log hour 89. This run was clean and spray dried.

F2-4-11

| # 2011 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 11 | 20110709 | 314682 | F2-4-11 | Seed | 120,000 | 114,700 | 29.11 | 27.82 | 69.03 |

FIGURE 1 CONTINUED (SL-F2-4-11) was inoculated on 7-01-11 from (G1A at log hour 52). 1100 liters of fed batch media was added over a 34 hour period between log hours 34-68. 32,047 lbs of glucose was added during this run. The harvest was started on 07-05-11 at log hour 86. This run was clean and spray dried.

F2-5-11

| #2011 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 13 | 20110718 | 314973 | F2-5-11 | Seed | 120,000 | 131,200 | 64.15 | 70.14 | 70.1 |

(SL-F2-5-11) was inoculated on 07-08-11 from (G1A at log hour 52). This run was batched to 110,000 liters with media based on 120,000 liters. 1100 liters of Fed batch media was added over a 38 hour period between log hours 24-62. 74,365 lbs of glucose was added during this run. Began chilling the vessel to 48°F at log hour 77. The harvest was started on 07-12-11 at log hour 82. This run was clean and spray dried.

F2-6-11

| #2011 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 14 | 20110725 | 315181 | F2-6-11 | Seed | 120,000 | 131000 | 57.19 | 62.43 | 73.55 |

(SL-F2-6-11) was inoculated on 07-15-11 from (G1 at log hour 84). This run was batched to 110,000 liters with media based on 120,000 liters. 1,100 liters of Fed batch media was added over a 37 hour period between log hours 25 and 62. 65,520 lbs of glucose was added during this run. Began chilling down to 48°F at log hour 67. The harvest was started on 07-18-11 at log hour 77. This run was clean and spray dried.

| #2011 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 16 | 20110804 | 315665 | F2-8-11 | Seed | 120,000 | 126,400 | 56.51 | 59.52 | 70.86 |

(SL-F2-8-11) was inoculated on 7-25-11 from (G1 at log hour 77). 1,000 liters of Fed batch media was added over a 30 hour period between log hours 24 -54. 61,576 lbs of glucose was added during this run. Started chilling the vessel to 48° F on 07-28-11 at log hour 61 due to contamination. Harvest was started on 07-28-11 at log hour. This run was clean and spray dried.

F2-9-11

| #2011 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 18 | 20110811 | 315869 | F2-9-11 | Seed | 120,000 | 133,200 | 59.54 | 66.09 | 76.89 |

(SL-F2-9-11) was inoculated on 8-03-11 from (G1A at log hour 89). 1200 liters of Fed batch media was added over a 40 hour period between log hours 24 -64. 74,300 lbs of glucose was added during this run. Stated chilling the vessel to 48° F on 08-06-11 at log hour 69. Harvest started at log hour 79. This was a clean run and Spray dried.

F2-10-11

| #2011 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 19 | 20110816 | 316416 | F2-10-11 | D/R | 120,000 | 131,500 | 50.98 | 55.87 | 72.15 |

(SL-F2-10-11) was inoculated on 8-08-11 from (G1 at log hour 769). 1200 liters of Fed batch media was added over a 37 hour period between log hours 24 -56. 70,906 lbs of glucose was added during this run. Starred chilling the vessel to 48° F on 08-11-11 at log hour 72. Harvest was started on 08-21-11 at log hour 79. This run was clean and spray dried.

| #2011 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 20 | 20110817 | 316266 | F1-8-11 | Seed | 80,000 | 87,000 | 70.40 | 76.56 | 76.31 |

(SL-F1-8-11) was inoculated on 8-11-11 from (G1A at log hour 77). 800 liters of Fed batch media was added over a 34 hour period between log hours 24 -58. 50,544 lbs of glucose was added during this run. Started chilling the vessel to 48° F on 08-11-11 at log hour 72. Harvest was started on 08-14-11 at log hour 89. This run was clean and spray dried.

F2-11-11

| #2011 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 21 | 20110822 | 316379 | F2-11-11 | Seed | 120,000 | 129,400 | 57.39 | 61.89 | 73.64 |

(SL-F2-11-11) was inoculated on 8-14-11 from (G1 at log hour 81). 1205.6 liters of Fed batch media was added over a 35 hour period between log hours 24- 59. 72,745 lbs of glucose was added during this run. Started chilling the vessel to 48° F on 08-17-11 at log hour 72. Harvest was started on 08-18-11 at log hour 82. This run was clean and spray dried.

F1-9-11

| #2011 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 22 | 20110823 | 316489 | F1-9-11 | Seed | 80,000 | 86000 | 76.18 | 81.89 | 75.57 |

FIGURE 1 CONTINUED (SL-F1-9-11) was inoculated on 8-18-11 from (G1A at log hour 69). 804 liters of Fed batch media was added over a 37 hour period between log hours 24- 61. 46,555 lbs. of glucose was added during this run. Started chilling the vessel to 48° F on 08-21-11 at log hour 72. Harvest was started on 08-22-11 at log hour 84. This run was clean and spray dried.

F2-13-11

| # 2011 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 25 | 20110908 | 316981 | SL F2-13-11 | Seed | 120,000 | 124,100 | 55.64 | 57.54 | 70.95 |

(SL-F2-13-11) was inoculated on 09-03-11 (from G1 @ log hour 80). 1208.6 liters of fed batch media was fed over a 34 hour period. 59,864 lbs. of glucose was fed over the duration of this run. Started chilling to 48 F on 09-06-11 at log hour 70. Started the harvest at log hour 84.

F2-14-11

| # 2011 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 28 | 20110920 | 317584 | F2-14-11 | Seed | 120,000 | 122,100 | 60.62 | 61.68 | 69.13 |

(SL-F2-14-11) was inoculated on 09-12-11 (from G1A @ log hour 77). 1207 liters of fed batch media was fed over a 38 hour period. 67,698 lbs. of glucose was fed over the duration of this run. Started chilling to 48 F on 09-16-11 at log hour 76. Started the harvest at log hour 84.

* Temperature deviation due to chilled water compressor failure (Vessel temperature reached 91 F).
* Lost air and buttoned up the fermenter due to chilled water compressor failure.

F1-13-11

| # 2011 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 29 | 20110922 | 317681 | F1-13-11 | Seed | 80,000 | 81,300 | 60.89 | 61.88 | 67.56 |

FIGURE 1 CONTINUED (SL-F1-13-11) was inoculated on 09-16-11 (from G1 @ log hour). 600 liters of fed batch media was fed over a 34 hour period. 27,732 lbs of glucose was fed over the duration of this run. Started chilling to 48 F on 09-19-11 at log hour 65. Started the harvest at log hour 74.

* Problems with fed batch flow control valve -- Changed diaphragm briefly exposing vessel -- No contamination detected during this run.
* Log hour 9 vessel heated to 93 F. Chilled water valve was closed due to control valve leaking by.

F1-14-11

| # 2011 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 31 | 20110928 | 317961 | F1-14-11 | Seed | 80,000 | 91,000 | 86.88 | 98.83 | 68.57 |

(SL-F1-14-11) was inoculated on 09-23-11 (from G1 @ log hour 64). 800 liters of fed batch media was fed over a 34 hour period. 45,590 lbs of glucose was fed over the duration of this run. Started chilling to 48 F on 09-26-11 at log hour 70. Started the harvest at log hour 83.

F3-4-11

| # 2011 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 32 | 20111003 | 318192 | SL F3-4-11 | Seed | 120,000 | 125,000 | 62.15 | 64.74 | 68.8 |

(SL-F3-4-11) was inoculated on 09-27-11 (from G1A @ log hour 90). 1205 liters of fed batch media was fed over a 34 hour period. 52,076 lbs of glucose was fed over the duration of this run. Started chilling to 48 F on 09-30-11 at log hour 70. Started the harvest at log hour 84.

* Foamed out approximately 4,500 liters at log 18.

F1-15-11

| # 2011 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 34 | 20111010 | 318457 | SL F1-15-11 | Seed | 80,000 | 86,100 | 89.83 | 96.67 | 70.58 |

FIGURE 1 CONTINUED (SL-F1-15-11) was inoculated on 10-05-11 (from G1 @ log hour 100). 800 liters of fed batch media was fed over a 34 hour period. 59,984 lbs. of glucose was fed over the duration of this run. Started chilling down on 10-0 -11 at log hour 70. Started the harvest at log hour 78.

- Modified media.
- Modified fed batch media.

F1-16-11

| # 2011 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 36 | 20111017 | 318716 | SL F1-16-11 | Seed | 80,000 | 85,400 | 74.26 | 79.27 | 72.72 |

(SL-F1-16-11) was inoculated on 10-10-11 (from G1 @ log hour 84.5). 800 liters of fed batch media was fed over a 34 hour period. 39,851 lbs of glucose was fed over the duration of this run. Started chilling down on 10-13-11 at log hour 70. Started the harvest at log hour 77.

- Modified media.
- Modified fed batch media.
- Normal fed batch media.

F3-8-11

| # 2011 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 46 | 20111111 | 319550 | SL F3-8-11 | Seed | 120,000 | 130,200 | 75.70 | 82.13 | 71.75 |

(SL-F3-8-11) was inoculated on 11-03-11 (from G1 @ log hour 94). 1200 liters of fed batch media was fed over a 34 hour period. 67,800 lbs of glucose was fed over the duration of this run. Started chilling to 48° F on 11-06-11 at log hour 75. Started the harvest at log hour 91.

| # 2011 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 48 | 20111115 | 319771 | SL F5-5-11 | Seed | 220,000 | 233,560 | 69.81 | 74.11 | 68.7 |

(SL-F5-5-11) was inoculated on 11-08-11 (from SV3 @ log hour 90). 2217 liters of fed batch media was fed over a 34 hour period. 45,836 liters of glucose was fed over the duration of this run. Started transferring 50% of F4 to F2 and chilling to 48° F on 11-11-11 at log hour 78. Started harvesting to centrifuges from F2 at log hour 88.

F3-14-11

| # 2011 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 63 | 20111222 | 321061 | SL F3-14-11 | Seed | 120,000 | 132,490 | 73.30 | 80.87 | 76.24 |

(SL-F3-14-11) was inoculated on 12-16-11 (from G1 @ log hour 106). 1202.7 liters of fed batch media was fed over a 34 hour period. 74,355 lbs of glucose was fed over the duration of this run. Started chilling to 48° F on 12-19-11 at log hour 72. Started the harvest at log hour 87.

* ph adjust chlorides with citric acid before filtering.

F1-25-11

| # 2011 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 64 | 20111223 | 321102 | SL F1-25-11 | Seed | 80,000 | 83,000 | 82.59 | 85.69 | 74.8 |

(SL-F1-25-11) was inoculated on 12-18-11 (from G1A @ log hour 91). 797.7 liters of fed batch media was fed over a 34 hour period. 43,673 lbs of glucose was fed over the duration of this run. Started chilling to 48° F on 12-21-11 at log hour 68. Started the harvest at log hour 94.

* ph adjusted chlorides before filtering.

| # 2011 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 66 | 20111228 | 321150 | SL-F3-15-11 | Seed | 120,000 | 131,000 | 71.15 | 77.67 | 75.8 |

(SL-F3-15-11) was inoculated on 12-23-11 (from G1 @ log hour 82). 1192.1 liters of fed batch media was fed over a 34 hour period. 76,953 lbs of glucose was fed over the duration of this run. Started chilling to 48° F on 12-26-11 at log hour 71. Started the harvest at log hour 85.

* ph adjust chlorides with citric acid before filtering.

F1-1-12

| # 2012 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 1 | 20120103 | 321175 | SL-F1-1-12 | Seed | 80,000 | 83,600 | 76.18 | 79.61 | 70.24 |

(SL-F1-1-12) was inoculated on 12-25-11 (from G1A @ log hour 69). 806.4 liters of fed batch media was fed over a 34 hour period. 40,847 lbs of glucose was fed over the duration of this run. Started chilling to 48° F on 12-28-11 at log hour 73. Started the harvest at log hour 85.

* ph adjusted chlorides before filtering.

F4-1-12

| # 2012 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 5 | 20120116 | 400538.1 | SL-F4-1-12 | Seed | 220,000 | 231,400 | 68.69 | 72.25 | 68.53 |

(SL-F4-1-12) was inoculated on 01-09-12 (from SV3 @ log hour). 2220.2 liters of fed batch media was fed over a 32 hour period. 42,343 liters of glucose was fed over the duration of this run. Started chilling to 48° F on 01-12-12 at log hour 74 and sending half to F2 to assist in chilling. Started centrifuging at log hour 79 from F4 first.

| #2012 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 6 | 20120120 | 400684.1 | SL-F6-2-12 | Seed | 216,000 | 237,200 | 76.27 | 83.76 | 69.13 |

(SL-F6-2-12) was inoculated on 01-12-12 (from SV3 @ log hour 43). 2223.4 liters of fed batch media was fed over a 32 hour period. 57,288 Liters of glucose was fed over the duration of this run. Started chilling to 48° F on 01-15-12 at log hour 85 and sending half to F2 to assist in chilling. Started centrifuging at log hour 89 from F6 first.

F5-2-12

| #2012 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 7 | 20120126 | 400940.1 | SL-F5-2-12 | Seed | 224,000 | 241,120 | 76.62 | 82.48 | 75 |

(SL-F5-2-12) was inoculated on 01-16-12 (from SL-F6-2-12 @ log hour 85). 2218.7 liters of fed batch media was fed over a 32 hour period. 55,998 liters of glucose was fed over the duration of this run. Started chilling to 48° F on 01-20-12 at log hour 97 and sending half to F2 to assist in chilling. Started centrifuging at log hour 117 from F5 first.

F4-2-12

| #2012 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 8 | 20120130 | 401149.1 | SL-F4-2-12 | Seed | 220,000 | 231,000 | 65.54 | 68.82 | 69.1 |

(SL-F4-2-12) was inoculated on 01-20-12 (from SV-3 @ log hour 47). 2215.4 liters of fed batch media was fed over a 32 hour period. 40,744 liters of glucose was fed over the duration of this run. Started chilling to 48° F on 01-23-12 at log hour 73. Started centrifuging at log hour 161.

FIGURE 1 CONTINUED

- Harvest was delayed due to the spray dryer issues.

F6-3-12

| # 2012 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 9 | 20120209 | 401534.1 | SL-F6-3-12 | Seed | 220,000 | 229,720 | 56.16 | 58.64 | 69.34 |

(SL-F6-3-12) was inoculated on 02-01-12 (from SV3 @ log hour 46). 2215.6 liters of fed batch media was fed over a 32 hour period. 35,494 liters of glucose was fed over the duration of this run. Started chilling and harvesting on 02-04-12 at log hour 78. Harvested straight to centrifuges at log hour 94 and did not use F2 as a harvest tank.

- Temperature excursion from log hour 13 to 21 due to temperature control in ROUT mode and not RCAS mode. Modifications were made to the procedure to ensure the temperature control is placed in RCAS mode when batching is started.

F5-3-12

| # 2012 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 10 | 20120215 | 401824.1 | SL-F5-3-12 | Seed | 220,000 | 224,300 | 59.62 | 60.79 | 67.28 |

(SL-F5-3-12) was inoculated on 02-07-12 (from SV3 @ log hour 46). 2214.9 liters of fed batch media was fed over a 32 hour period. 36,746 liters of glucose was fed over the duration of this run. Started chilling and harvesting on 02-11-12 at log hour 93. Harvested straight to centrifuges and did not use F2 as a harvest tank.

F1-2-12

| # 2012 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 11 | 20120229 | 402398.1 | SL-F1-2-12 | Seed | 80,000 | 83,600 | 89.65 | 93.68 | 71.89 |

FIGURE 1 CONTINUED (SL-F1-2-12) was inoculated on 02-22-12 (from G1 @ log hour 54). 797.9 liters of fed batch media was fed over a 32 hour period. 48,871 lbs of glucose was fed over the duration of this run. Started chilling to 48° F on 12-28-11 at log hour 72. Started the harvest at log hour 81.

F1-4-12

| #2012 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 18 | 20120328 | 404340.1 | SL-F1-4-12 | Seed | 80,000 | 89,200 | 90.29 | 100.67 | 68.42 |

(SL-F1-4-12) was inoculated on 03-22-12 (from G1 @ log hour 71). 893.6 liters of fed batch media was fed over a 34 hour period. 59,067 lbs of glucose was fed over the duration of this run. Started chilling to 48° F on 03-25-12 at log hour 72. Started centrifuging at log hour 83.

F3-4-12

| #2012 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 27 | 20120501 | 404568.1 | SL-F3-4-12 | Seed | 120,000 | 129,200 | 85.00 | 91.52 | 70.93 |

(SL-F3-4-12) was inoculated on 04-25-12 (from G1 @ log hour 67). 1193.8 liters of fed batch media was fed over a 34 hour period. 92,224 lbs of glucose was fed over the duration of this run. Started chilling to 48° F on 04-28-12 at log hour 72. Started centrifuging at log hour 89.

F6-7-12

| #2012 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 28 | 20120507 | 404695.1 | SL-F6-7-12 | Seed | 220,000 | 241,580 | 73.37 | 80.57 | 70.95 |

(SL-F6-7-12) was inoculated on 04-27-12 (from SV-3 @ log hour 77). 2217.2 liters of fed batch media was fed over a 34 hour period. 53,951 of glucose was fed over the duration of this run. Started chilling to 48° F on 04-30-12 at log hour 81. Started centrifuging at log hour 108.

| #2012 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 29 | 20120508 | 404849.1 | SL-F1-8-12 | Seed | 80,000 | 89,300 | 89.04 | 99.39 | 72.08 |

(SL-F1-8-12) was inoculated on 04-30-12 (from G1A @ log hour 74). 53,393 lbs of glucose was fed over the duration of this run. Started chilling to 48° F on 05-03-12 at log hour 72. 795.5 liters of fed batch media was fed over a 34 hour period. Started centrifuging at log hour 122.

- Run using antifoam ESP FC 131. It appeared to work well in F1.
- Problems occurred spray drying. The product was very sticking and not flowing well. 260 kilos of oily clumps was lost in the sifter overflow. The product from the sifter overflow could not be recovered. The dryer also had an oily product build up.

F3-6-12

| #2012 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 31 | 20120525 | 405450.1 | SL-F3-6-12 | Seed | 120,000 | 123,800 | 74.09 | 76.44 | 72.15 |

(SL-F3-6-12) was inoculated on 05-18-12 (from G1 @ log hour 89). 1201.5 liters of fed batch media was fed over a 34 hour period. 78,211 lbs of glucose was fed over the duration of this run. Started chilling to 48° F on 05-21-12 at log hour 72. Started centrifuging at log hour 84.

- Using ESP FC 131 Antifoam.

F3-7-12

| #2012 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 32 | 20120531 | 405587.1 | SL-F3-7-12 | Seed | 120,000 | 126,800 | 78.12 | 82.55 | 69.63 |

(SL-F3-7-12) was inoculated on 05-24-12 (from G1 @ log hour 72). 1197 liters of fed batch media was fed over a 34 hour period. 80,494 lbs of glucose was fed over the duration of this run. Started chilling to 48° F on 05-21-12 at log hour 72. Started centrifuging at log hour 83.

FIGURE 1 CONTINUED

- Using ESP FC 131 Antifoam.
- Foam out around log hour 15-16. Lost approximately 2,000 liter.
- Lost unknown amount during harvest due to CT-2 sample port being left open. NCR issued.

F3-8-12

| # 2012 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 33 | 20120605 | 405739.1 | SL-F3-8-12 | Seed | 120,000 | 126,900 | 66.06 | 69.86 | 71.77 |

(SL-F3-8-12) was inoculated on 05-30-12 (from G1A @ log hour 73). 1209 liters of fed batch media was fed over a 34 hour period. 70,747 lbs of glucose was fed over the duration of this run. Started chilling to 48° F on 06-02-12 at log hour 72. Started centrifuging at log hour 81.

F3-9-12

| # 2012 | DATE POSTED | PROD ORDER # | VESSEL/ RUN# | Origin | Batch Volume (L) | Final Tank Volume(L) | BIOMASS g/L | Volume Adjusted g/L | % FAT |
|---|---|---|---|---|---|---|---|---|---|
| 34 | 20120612 | 405946.1 | SL-F3-9-12 | Seed | 120,000 | 131,900 | 79.18 | 87.03 | 69.18 |

(SL-F3-9-12) was inoculated on 06-05-12 (from G1 @ log hour 73). 1199.5 liters of fed batch media was fed over a 34 hour period. 87,424 lbs of glucose was fed over the duration of this run. Started chilling to 48° F on 06-05-12 at log hour 72. Started centrifuging at log hour 86.

FIGURE 2 a) <u>F1-2-11</u>

| F1-2-11 | |
|---|---|
| FATTY ACID PROFILE | |
| TEST | RESULTS |
| C 06:0 (Caproic acid) | <0.10 % |
| C 07:0 (Heptanoic acid) | <0.10 % |
| C 08:0 (Caprylic acid) | <0.10 % |
| C 09:0 (Nonanoic acid) | <0.10 % |
| C 10:0 (Capric acid) | <0.10 % |
| C 11:0 (Undecanoic acid) | <0.10 % |
| C 12:0 (Lauric acid) | <0.10 % |
| C 13:0 (Tridecanoic acid) | <0.10 % |
| C 14:0 (Myristic acid) | 4.01% |
| C 14:1 (Myristoleic acid) | 1.35% |
| C 15:0 (Pentadecanoic acid) | <0.10 % |
| C 15:1 (Pentadecenoic acid) | <0.10 % |
| C 16:0 (Palmitic acid) | 54.42% |
| C 16:1 (Palmitoleic acid) | <0.10 % |
| C 17:0 (Margaric acid) | 0.51% |
| C 17:1 (Margaroleic acid) | <0.10 % |
| C 18:0 (Stearic acid) | 1.81% |
| C 18:1n7 (Vaccenic acid) | <0.10 % |
| C 18:1n9 (Oleic acid) | <0.10 % |
| C 18:1n9t (Elaidic acid) | <0.10 % |
| C 18:2n6 (Linoleic acid) | <0.10 % |
| C 18:2n6t (Linolelaidic acid) | <0.10 % |
| C 18:3n3 (alpha-Linolenic) | <0.10 % |
| C 18:3n6 (gamma-Linolenic) | <0.10 % |
| C 19:0 (Nonadecanoic acid) | <0.10 % |
| C 20:0 (Arachidic acid) | 0.31% |
| C 20:1 (Eicosenoic acid) | <0.10 % |
| C 20:2n6 (Eicosadienoic acid) | <0.10 % |
| C 20:3n3 (Eicosatrienoic acid) | <0.10 % |
| C 20:3n6 (homo-gamma-Linolenic acid) | <0.10 % |
| C 20:4n6 (Arachidonic acid) | <0.10 % |
| C 20:5n3 (Eicosapentaenoic acid) | 0.37% |
| C 21:0 (Heneicosanoic acid) | <0.10 % |
| C 22:0 (Behenic acid) | 0.18% |
| C 22:1 (Erucic acid) | 0.63% |
| C 22:2n6 (Docosadienoic acid) | 0.45% |

FIGURE 2 CONTINUED

| | |
|---|---|
| C 22:5n3 (Docosapentaenoic acid) | <0.10 % |
| C 22:6n3 (Docosahexaenoic acid) | 27.22% |
| C 23:0 (Tricosanoic acid) | <0.10 % |
| C 24:0 (Lignoceric acid) | <0.10 % |
| C 24:1 (Nervonic acid) | <0.10 % |
| Unknown Components | 0.95% | b) <u>F1-9-11</u>

| F1-9-11 | |
|---|---|
| FATTY ACID PROFILE | |
| TEST | RESULTS |
| C 06:0 (Caproic acid) | <0.10 % |
| C 07:0 (Heptanoic acid) | <0.10 % |
| C 08:0 (Caprylic acid) | <0.10 % |
| C 09:0 (Nonanoic acid) | <0.10 % |
| C 10:0 (Capric acid) | <0.10 % |
| C 11:0 (Undecanoic acid) | <0.10 % |
| C 12:0 (Lauric acid) | <0.10 % |
| C 13:0 (Tridecanoic acid) | <0.10 % |
| C 14:0 (Myristic acid) | 4.15% |
| C 14:1 (Myristoleic acid) | 1.51% |
| C 15:0 (Pentadecanoic acid) | <0.10 % |
| C 15:1 (Pentadecenoic acid) | <0.10 % |
| C 16:0 (Palmitic acid) | 55.50% |
| C 16:1 (Palmitoleic acid) | <0.10 % |
| C 17:0 (Margaric acid) | 0.53% |
| C 17:1 (Margaroleic acid) | <0.10 % |
| C 18:0 (Stearic acid) | 1.77% |
| C 18:1n7 (Vaccenic acid) | <0.10 % |
| C 18:1n9 (Oleic acid) | <0.10 % |
| C 18:1n9t (Elaidic acid) | <0.10 % |
| C 18:2n6 (Linoleic acid) | <0.10 % |
| C 18:2n6t (Linolelaidic acid) | <0.10 % |
| C 18:3n3 (alpha-Linolenic) | <0.10 % |
| C 18:3n6 (gamma-Linolenic) | <0.10 % |
| C 19:0 (Nonadecanoic acid) | <0.10 % |
| C 20:0 (Arachidic acid) | 0.30% |
| C 20:1 (Eicosenoic acid) | <0.10 % |
| C 20:2n6 (Eicosadienoic acid) | <0.10 % |
| C 20:3n3 (Eicosatrienoic acid) | <0.10 % |
| C 20:3n6 (homo-gamma-Linolenic acid) | <0.10 % |

FIGURE 2 CONTINUED

| | |
|---|---|
| C 20:4n6 (Arachidonic acid) | <0.10 % |
| C 20:5n3 (Eicosapentaenoic acid) | 0.13% |
| C 21:0 (Heneicosanoic acid) | <0.10 % |
| C 22:0 (Behenic acid) | <0.10 % |
| C 22:1 (Erucic acid) | 0.58% |
| C 22:2n6 (Docosadienoic acid) | 0.43% |
| C 22:5n3 (Docosapentaenoic acid) | <0.10 % |
| C 22:6n3 (Docosahexaenoic acid) | 27.03% |
| C 23:0 (Tricosanoic acid) | <0.10 % |
| C 24:0 (Lignoceric acid) | <0.10 % |
| C 24:1 (Nervonic acid) | <0.10 % |
| Unknown Components | 0.57% | c) <u>F1-5-11</u>

| F1-5-11 | |
|---|---|
| FATTY ACID PROFILE | |
| TEST | RESULTS |
| C 06:0 (Caproic acid) | <0.10 % |
| C 07:0 (Heptanoic acid) | <0.10 % |
| C 08:0 (Caprylic acid) | <0.10 % |
| C 09:0 (Nonanoic acid) | <0.10 % |
| C 10:0 (Capric acid) | <0.10 % |
| C 11:0 (Undecanoic acid) | <0.10 % |
| C 12:0 (Lauric acid) | <0.10 % |
| C 13:0 (Tridecanoic acid) | <0.10 % |
| C 14:0 (Myristic acid) | 3.42% |
| C 14:1 (Myristoleic acid) | 1.92% |
| C 15:0 (Pentadecanoic acid) | <0.10 % |
| C 15:1 (Pentadecenoic acid) | <0.10 % |
| C 16:0 (Palmitic acid) | 54.15% |
| C 16:1 (Palmitoleic acid) | <0.10 % |
| C 17:0 (Margaric acid) | 0.85% |
| C 17:1 (Margaroleic acid) | <0.10 % |
| C 18:0 (Stearic acid) | 1.80% |
| C 18:1n7 (Vaccenic acid) | <0.10 % |
| C 18:1n9 (Oleic acid) | <0.10 % |
| C 18:1n9t (Elaidic acid) | <0.10 % |
| C 18:2n6 (Linoleic acid) | <0.10 % |
| C 18:2n6t (Linolelaidic acid) | <0.10 % |
| C 18:3n3 (alpha-Linolenic) | <0.10 % |
| C 18:3n6 (gamma-Linolenic) | <0.10 % |

FIGURE 2 CONTINUED

| | |
|---|---|
| C 19:0 (Nonadecanoic acid) | <0.10 % |
| C 20:0 (Arachidic acid) | 0.23% |
| C 20:1 (Eicosenoic acid) | <0.10 % |
| C 20:2n6 (Eicosadienoic acid) | <0.10 % |
| C 20:3n3 (Eicosatrienoic acid) | <0.10 % |
| C 20:3n6 (homo-gamma-Linolenic acid) | <0.10 % |
| C 20:4n6 (Arachidonic acid) | <0.10 % |
| C 20:5n3 (Eicosapentaenoic acid) | 0.33% |
| C 21:0 (Heneicosanoic acid) | <0.10 % |
| C 22:0 (Behenic acid) | <0.10 % |
| C 22:1 (Erucic acid) | 0.38% |
| C 22:2n6 (Docosadienoic acid) | 0.42% |
| C 22:5n3 (Docosapentaenoic acid) | <0.10 % |
| C 22:6n3 (Docosahexaenoic acid) | 27.34% |
| C 23:0 (Tricosanoic acid) | <0.10 % |
| C 24:0 (Lignoceric acid) | <0.10 % |
| C 24:1 (Nervonic acid) | <0.10 % |
| Unknown Components | 0.62% | d) <u>F1-14-11</u>

| F1-14-11 ||
|---|---|
| FATTY ACID PROFILE ||
| TEST | RESULTS |
| C 06:0 (Caproic acid) | <0.10 % |
| C 07:0 (Heptanoic acid) | <0.10 % |
| C 08:0 (Caprylic acid) | <0.10 % |
| C 09:0 (Nonanoic acid) | <0.10 % |
| C 10:0 (Capric acid) | <0.10 % |
| C 11:0 (Undecanoic acid) | <0.10 % |
| C 12:0 (Lauric acid) | 0.17% |
| C 13:0 (Tridecanoic acid) | <0.10 % |
| C 14:0 (Myristic acid) | 4.57% |
| C 14:1 (Myristoleic acid) | <0.10 % |
| C 15:0 (Pentadecanoic acid) | 1.44% |
| C 15:1 (Pentadecenoic acid) | <0.10 % |
| C 16:0 (Palmitic acid) | 53.49% |
| C 16:1 (Palmitoleic acid) | 0.14% |
| C 17:0 (Margaric acid) | 0.45% |
| C 17:1 (Margaroleic acid) | <0.10 % |
| C 18:0 (Stearic acid) | 1.67% |
| C 18:1n7 (Vaccenic acid) | <0.10 % |

FIGURE 2 CONTINUED

| | |
|---|---|
| C 18:1n9 (Oleic acid) | 0.11% |
| C 18:1n9t (Elaidic acid) | <0.10 % |
| C 18:2n6 (Linoleic acid) | <0.10 % |
| C 18:2n6t (Linolelaidic acid) | <0.10 % |
| C 18:3n3 (alpha-Linolenic) | <0.10 % |
| C 18:3n6 (gamma-Linolenic) | <0.10 % |
| C 19:0 (Nonadecanoic acid) | <0.10 % |
| C 20:0 (Arachidic acid) | 0.31% |
| C 20:1 (Eicosenoic acid) | <0.10 % |
| C 20:2n6 (Eicosadienoic acid) | <0.10 % |
| C 20:3n3 (Eicosatrienoic acid) | <0.10 % |
| C 20:3n6 (homo-gamma-Linolenic acid) | 0.15% |
| C 20:4n6 (Arachidonic acid) | 0.86% |
| C 20:5n3 (Eicosapentaenoic acid) | 0.31% |
| C 21:0 (Heneicosanoic acid) | <0.10 % |
| C 22:0 (Behenic acid) | 0.17% |
| C 22:1 (Erucic acid) | <0.10 % |
| C 22:2n6 (Docosadienoic acid) | <0.10 % |
| C 22:5n3 (Docosapentaenoic acid) | <0.10 % |
| C 22:6n3 (Docosahexaenoic acid) | 27.33% |
| C 23:0 (Tricosanoic acid) | <0.10 % |
| C 24:0 (Lignoceric acid) | 0.14% |
| C 24:1 (Nervonic acid) | 0.22% |
| Unknown Components | 1.42% | e) F1-15-11

| F1-15-11 | |
|---|---|
| FATTY ACID PROFILE | |
| TEST | RESULTS |
| C 06:0 (Caproic acid) | <0.10 % |
| C 07:0 (Heptanoic acid) | <0.10 % |
| C 08:0 (Caprylic acid) | <0.10 % |
| C 09:0 (Nonanoic acid) | <0.10 % |
| C 10:0 (Capric acid) | <0.10 % |
| C 11:0 (Undecanoic acid) | <0.10 % |
| C 12:0 (Lauric acid) | 0.16% |
| C 13:0 (Tridecanoic acid) | <0.10 % |
| C 14:0 (Myristic acid) | 4.43% |
| C 14:1 (Myristoleic acid) | 0.18% |
| C 15:0 (Pentadecanoic acid) | 1.17% |
| C 15:1 (Pentadecenoic acid) | <0.10 % |

FIGURE 2 CONTINUED

| | |
|---|---|
| C 16:0 (Palmitic acid) | 55.87% |
| C 16:1 (Palmitoleic acid) | 0.13% |
| C 17:0 (Margaric acid) | 0.40% |
| C 17:1 (Margaroleic acid) | <0.10 % |
| C 18:0 (Stearic acid) | 1.62% |
| C 18:1n7 (Vaccenic acid) | <0.10 % |
| C 18:1n9 (Oleic acid) | <0.10 % |
| C 18:1n9t (Elaidic acid) | <0.10 % |
| C 18:2n6 (Linoleic acid) | <0.10 % |
| C 18:2n6t (Linolelaidic acid) | <0.10 % |
| C 18:3n3 (alpha-Linolenic) | <0.10 % |
| C 18:3n6 (gamma-Linolenic) | <0.10 % |
| C 19:0 (Nonadecanoic acid) | <0.10 % |
| C 20:0 (Arachidic acid) | 0.28% |
| C 20:1 (Eicosenoic acid) | <0.10 % |
| C 20:2n6 (Eicosadienoic acid) | <0.10 % |
| C 20:3n3 (Eicosatrienoic acid) | 0.90% |
| C 20:3n6 (homo-gamma-Linolenic acid) | 0.13% |
| C 20:4n6 (Arachidonic acid) | <0.10 % |
| C 20:5n3 (Eicosapentaenoic acid) | 0.29% |
| C 21:0 (Heneicosanoic acid) | <0.10 % |
| C 22:0 (Behenic acid) | 0.15% |
| C 22:1 (Erucic acid) | <0.10 % |
| C 22:2n6 (Docosadienoic acid) | 0.43% |
| C 22:5n3 (Docosapentaenoic acid) | <0.10 % |
| C 22:6n3 (Docosahexaenoic acid) | 26.92% |
| C 23:0 (Tricosanoic acid) | <0.10 % |
| C 24:0 (Lignoceric acid) | <0.10 % |
| C 24:1 (Nervonic acid) | 0.22% |
| Unknown Components | 0.65% |

FIGURE 3

ALLTECH QUALITY ASSURANCE LABORATORIES

Typical Fatty Acid Profile of ALGAE-S Meal

| Fatty Acid | % of Fat content |
|---|---|
| Caproic Acid | <0.10% |
| Heptanoic Acid | <0.10% |
| Caprylic Acid | <0.10% |
| Nonanoic Acid | <0.10% |
| Capric Acid | <0.10% |
| Undecanoic Acid | <0.10% |
| Lauric Acid | <0.10% |
| Tridecanoic Acid | <0.10% |
| Myristic Acid | 3.86% |
| Myristoleic Acid | 1.60% |
| Pentadecanoic Acid | <0.10% |
| Palmitic Acid | 54.69% |
| Palmitoleic Acid | <0.10% |
| Margaric Acid | 0.63% |
| Margaroleic Acid | <0.10% |
| Stearic Acid | 1.80% |
| Vaccenic Acid | <0.10% |
| Oleic Acid | <0.10% |
| Elaidic Acid | <0.10% |
| Linoleic Acid | <0.10% |
| Linolelaidic Acid | <0.10% |
| Alpha-Linoleic Acid | <0.10% |
| Gamma-Linoleic Acid | <0.10% |
| Nonadecanoic Acid | <0.10% |
| Arachidic Acid | 0.28% |
| Eicosenoic Acid | <0.10% |
| Eicosadienoic Acid | <0.10% |
| Eicosatrienoic Acid | <0.10% |
| Homo-gamma-Linoleic Acid | <0.10% |
| Arachidonic Acid | <0.10% |
| Eicosapentaenoic Acid | 0.28% |
| Heneicosanoic Acid | <0.10% |
| Behenic Acid | <0.10% |
| Erucic Acid | 0.53% |
| Docosadienoic Acid | 0.43% |
| Docosapentaenoic Acid | <0.10% |
| Docosahexaenoic Acid | 27.20% |
| Tricosanoic Acid | <0.10% |
| Lignoceric Acid | <0.10% |
| Nervonic Acid | <0.10% |
| Unknown | 0.71% |

ALGAL LIPID COMPOSITIONS AND METHODS OF PREPARING AND UTILIZING THE SAME

This application claims priority to U.S. Provisional Patent Application Ser. No. 61/507,390 filed 13 Jul. 2011, hereby incorporated by reference in its entirety.

FIELD OF THE INVENTION

This invention relates to compositions comprising high lipid content algae and methods of making and utilizing the same. In particular, the invention relates to high lipid content algae biomass and algal lipid materials derived from the same, methods of making the same, as well as to biofuels (e.g., biodiesel) and dietary compositions (e.g., animal feeds) comprising or made from the same. Compositions and methods of the invention find use in a variety of applications including biofuel, dietary (e.g., human and animal nutrition), therapeutic as well as research applications.

BACKGROUND OF THE INVENTION

Within the last several years, the production of biofuel (e.g., biodiesel) from algae has been an area of interest. In part, this is due to high quality agricultural land not being required to grow algae (algal biomass). However, commercial production of biofuel (e.g., biodiesel) from algae has remained a challenge.

In addition, over the fast fifty years, approaches toward providing animal nutrition have changed. No longer are animals fed whatever forage or other material that may be available. Instead, the diets of animals are closely monitored for total nutrition value and cost. Very often, animals on specific diets are monitored for quality and performance characteristics with the nutritional components of the feed being adjusted to maximize nutrition value of the feed and optimization of animal performance characteristics.

However, cost is a critical factor. There is a continual search for cost-effective animal feeds, not only to sustain animals, but in many cases to cause enhanced growth and value.

SUMMARY OF THE INVENTION

The invention relates to compositions comprising high lipid content algae and methods of making and utilizing the same. In particular, the invention relates to high lipid content algae biomass and algal lipid materials derived from the same, methods of making the same, as well as to biofuels (e.g., biodiesel) and dietary compositions (e.g., animal feeds) comprising or made from the same. Compositions and methods of the invention find use in a variety of applications including biofuel, dietary (e.g., human and animal nutrition), therapeutic as well as research applications.

Accordingly, the invention provides a process of making an algal biomass comprising a desired, high fat content (e.g., at least 67% total fat) comprising culturing an algae under culture conditions sufficient to provide an algal biomass comprising a desired, high fat content. The invention has identified culture conditions under which it is possible to obtain an algal biomass comprising a desired level of total fat (e.g., at least 67% total fat). The invention is not limited to the total fat content (e.g., by weight) of an algal biomass generated according to the invention. In a preferred embodiment, an algal biomass generated and/or used according to the invention comprises a fat content of at least 67% by weight. However, the invention also provides compositions and methods of generating an algal biomass containing greater (e.g., greater than 68%, greater than 69%, greater than 70%, greater than 71%, greater than 72%, greater than 73%, greater than 74%, greater than 75%, greater than 76%, greater than 77%, greater than 78%, greater than 79%, greater than 80%, greater than 81%, greater than 82%, greater than 85%, or more) or lesser (e.g., about 66%, about 65%, about 64%), about 63%, about 62%, about 61%, about 60%, about 59%, about 58%, about 57%, about 56%, about 55%, about 54%, or less) amount of total fat. Indeed, methods and compositions described herein can be utilized to generate an algal biomass containing any desired level of total fat content. In some embodiments, the algae biomass is cultured in two or more types of culture medium in a sequential manner. For example, in some embodiments, one culture medium of the two or more culture medium contains 50 g/L of a carbon source, about 7.5 g/L yeast extract, about 0.15 g/L magnesium sulfate, about 0.15 g/L calcium chloride and 0.15 g/L magnesium chloride. The invention is not limited by the carbon source. Indeed, a variety of carbon sources may be used including, but not limited to, carbohydrates such as glucose, fructose, xylose, saccharose, maltose or soluble starch as well as oleic acid, fats such as soybean oil, molasses, glycerol, mannitol, and sodium acetate, cotton seed flour, glycerol, molasses and corn steep liquor. In some embodiments, another culture medium of the two or more culture medium contains 50 g/L of a carbon source, about 7.5 g/L yeast extract, about 4.0 g/L magnesium sulfate, about 1 g/L urea, about 2 g/L calcium chloride, about 2 g/L magnesium chloride and about 0.25 g/L monopotassium phosphate. In some embodiments, one culture medium of the two or more culture medium contains a carbon source, yeast extract and sea salt. In some embodiments, and as described herein, algae are cultured in a first culture medium (e.g., containing glucose, yeast extract and sea salt); transferred into and incubated in a second culture medium (e.g., containing glucose, yeast extract, magnesium sulfate, calcium chloride and magnesium chloride); and transferred into and incubated in a third culture medium (e.g., containing glucose, yeast extract, magnesium sulfate, urea, calcium chloride, magnesium chloride and monopotassium phosphate). In some embodiments, one of the culture mediums is supplemented with a fed-batch feed. In a preferred embodiment, the third culture medium is supplemented with a fed-batch feed. The invention is not limited by the type, or duration, of fed-batch feed utilized. In some embodiments, the fed-batch feed comprises urea and monopotassium phosphate. The invention is not limited by the amounts and/or ratios of media components used in the cultures. Examples that may be utilized as components of each of the various media (e.g., first culture media, second culture media, batch media and fed-batch media) are described in detail herein. In some embodiments, the algal biomass is harvested from a culture (e.g., from a third culture medium) between 12-24 hours after cessation of the fed-batch process. In some embodiments, the algal biomass is harvested from the third culture medium after all of the nutrients have been removed/consumed from the medium. The invention is not limited by the way in which the algal biomass is harvested. Indeed, a variety of ways may be used to harvest the biomass including, but not limited to, the methods described herein. In some embodiments, the algal biomass is harvested via centrifugation. In some embodiments, the culture medium comprising the algal biomass is chilled prior to harvesting the algal biomass. The invention is not limited by the temperature to which the culture medium comprising the algal biomass is chilled prior to harvesting. Indeed, a variety of temperatures may be used including, but not limited to, those described herein. In some embodiments, the culture medium comprising the algal biomass is chilled to between about 5 and 25 C. The invention is not limited by the type of algae used in the invention. Indeed, a variety of algae may be used (e.g., independently or in combination) including, but not limited to, those described herein. In some embodiments, the algae is a strain or species from the genus *Chlorella*, the genus *Schizochytrium*, or the genus *Crypthecodinium*. In a preferred embodiment, the algae is *Schizochytrium limacinum*. In some embodiments, the first culture medium contains about 50 g/L glucose, about 10 g/L yeast extract and about 4 g/L sea salt. In some embodiments, the second culture medium contains about 50 g/L glucose, about 7.5 g/L yeast extract, about 0.15 g/L magnesium sulfate, about 0.15 g/L calcium chloride and 0.15 g/L magnesium chloride. In some embodiments, the third culture medium contains about 50 g/L glucose, about 7.5 g/L yeast extract, about 4.0 g/L magnesium sulfate, about 1 g/L urea, about 2 g/L calcium chloride, about 2 g/L magnesium chloride and about 0.25 g/L monopotassium phosphate, in some embodiments, the culture conditions comprise running the algae culture at 30 C under airflow and agitation conditions so as to maintain dissolved oxygen at about 10%. In some embodiments, the third culture medium (e.g., the culture media present at the time of inoculation of a main fermentor (e.g., 70,000 L, 120,000 L, 256,000 L vessel)) contains medium with an initial ratio of nitrogen (N):phosphorus (P):potassium (K) of 46:13:8.5. In a preferred embodiment, the N:P:K ratio is the same in the batch and fed-batch culture modes. In some embodiments, the ratio of magnesium (Mg):calcium (Ca) is 3:1 in culture media used in both batch and fed-batch modes, although higher (e.g., 4:1, 4.5:1, or more) and lower (e.g., 2.5:1, 2:1, 1.5:1, or lower) ratios may be used. In another embodiment, the ratio of chloride (Cl2):sulfate (SO4)) of 1:1 is used in culture media used in both batch and fed-batch modes, although higher (e.g., 2:1, 3:1, 4:1, 5:1, or more) and lower (e.g., 1:2, 1:3, 1:4, 1:5, or lower) ratios may be used. In some embodiments, the ratio of sulfate (SO4):phosphate (PO4) in media at the time of inoculation of a main fermentor (e.g., 70,000 L, 120,000 L, 256,000 L vessel) is 16:1, although higher (e.g., 20:1, 25:1, 30:1, 32:1, or more) and lower (e.g., 10:1, 8:1, 5:1, 3:1, or lower) ratios may be used. In some embodiments, the total ratio of sulfate (SO4):phosphate (PCM) that has been batched and fed at the end of a full culture (e.g., including inoculum, first seed stage, second seed stage and main fermentor cultures) that generates an algal biomass containing a desired fat content (e.g., greater than 67% fat) is 5.3:1, although higher (e.g., 5.5:1, 5.7:1, 6:1, 7:1, 8:1 or higher) and lower (e.g., 5:1, 4.5:1, 4:1, 3:1, or lower) ratios may be used. In some embodiments, the ratio of chloride (Cl2):phosphate (PCM) in media at the time of inoculation of a main fermentor (e.g., 70,000 L, 120,000 L, 256,000 L vessel) is 16:1, although higher (e.g., 20:1, 25:1, 30:1, 32:1, or more) and lower (e.g., 10:1, 8:1, 5:1, 3:1, or lower) ratios may be used. In some embodiments, the total ratio of chloride (Cl2):phosphate (PCM) that has been batched and fed at the end of a full culture (e.g., including inoculum, first seed stage, second seed stage and main fermentor cultures) that generates an algal biomass containing a desired fat content (e.g., greater than 67% fat) is 5.3:1, although higher (e.g., 5.5:1, 5.7:1, 6:1, 7:1, 8:1 or higher) and lower (e.g., 5:1, 4.5:1, 4:1, 3:1, or lower) ratios may be used.

The invention also provides an algal biomass having a desired, high fat content (e.g., total fat content of at least 67% by weight). In some embodiments, the biomass comprises about 170-250 mg/g docosahexaenoic acid (DHA) and/or about 150-400 mg/g palmitic acid. In some embodiments, the invention provides a lipid composition, a food product or other material comprising the algal biomass (e.g., dried algal biomass) or a component thereof (e.g., a fatty acid component thereof). In some embodiments, the algal biomass (e.g., a dried algal biomass (e.g., generated according to a method described herein)) contains a desired amount of total fat and/or other components (e.g. greater than about 68% total fat, greater than about 69% total fat, greater than about 70% total fat, greater than about 71% total fat, greater than about 72% total fat, greater than about 73% total fat, greater than about 74% total fat, greater than about 75% total fat, greater than about 76% total fat, greater than about 77% total fat, or greater than about 78% total fat). In some embodiments, an algal biomass of the invention (e.g., containing greater than 67% total fat) is dried such that the biomass contains less than 5% moisture (e.g., less than 4.5% moisture, less than 4% moisture, less than 3.5% moisture, less than 3% moisture, less than 2.5% moisture, less than 2% moisture, or less than 1.5% moisture). In some embodiments, an algal biomass of the invention (e.g., a dried biomass containing less than 5% moisture) contains about 170-250 mg/g or more docosahexaenoic acid (DHA) (e.g., about 170-180 mg/g DHA, about 180-190 mg/g DHA, about 190-200 mg/g DHA, about 200-210 mg/g DHA, about 210-220 mg/g DHA, about 220-230 mg/g DHA, about 230-240 mg/g DHA, about 240-250 mg/g DHA, or more than 250 mg/g DHA). In some embodiments, an algal biomass of the invention (e.g., a dried biomass containing less than 5% moisture) contains about 150-400 mg/g or more palmitic acid (IUPAC name: hexadecanoic acid (e.g., about 150-200 mg/g, about 200-225 mg/g, about 225-250 mg/g, about 250-275 mg/g, about 275-300 mg/g, about 300-325 mg/g, about 325-350 mg/g, about 350-375 mg/g, about 375-400 mg/g, or more than 400 mg/g)). In some embodiments, an algal biomass of the invention (e.g., a dried biomass containing less than 5% moisture) contains about 300-600 mg/g or more total fatty acids (e.g., about 300-350 mg/g, about 350-400 mg/g, about 400-450 mg/g, about 450-500 mg/g, about 500-550 mg/g, about 550-600 mg/g, or more than 600 mg/g fatty acids)). In some embodiments, an algal biomass of the invention (e.g., a dried biomass containing less than 5% moisture) contains less than about 15% protein (e.g., less than about 14% protein, less than about 13% protein, less than about 12% protein, less than about 11% protein, less than about 10% protein, less than about 9% protein, or less than about 8% protein). In some embodiments, an algal biomass or component thereof of the invention is used in preparing biofuel (e.g., biodiesel). In some embodiments, an algal biomass or component thereof of the invention is used in preparing a food product (e.g., an animal feed or feed component).

BRIEF DESCRIPTION OF THE DRAWINGS

FIG. 1 depicts data generated during large scale, heterotrophic algae biomass production according to aspects of the invention.

FIG. 2 shows the fatty acid profile of algae biomass harvested from several, independent large scale algal cultures.

FIG. 3 shows a composite fatty acid profile of a harvested biomass utilizing materials and methods described herein.

DEFINITIONS

As used herein, "phospholipid" refers to an organic compound having the following general structure:

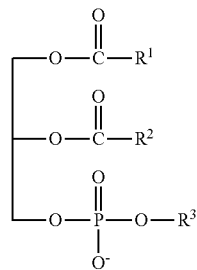

wherein R1 is a fatty acid residue, R2 is a fatty acid residue or —OH, and R3 is a —H or nitrogen containing compound choline ($HOCH_2CH_2CH_2N^+(CH_3)_3OH^-$), ethanolamine ($HOCH_2CH_2NH_2$), inositol or serine. R1 and R2 cannot simultaneously be OH. When R3 is an —OH, the compound is a diacylglycerophosphate, while when R3 is a nitrogen-containing compound, the compound is a phosphatide such as lecithin, cephalin, phosphatidyl serine or plasmalogen.

An "ether phospholipid" as used herein refers to a phospholipid having an ether bond at position 1 the glycerol backbone. Examples of ether phospholipids include, but are not limited to, alkylacylphosphatidylcholine (AAPC), lyso-alkylacylphosphatidylcholine (LAAPC), and alkylacylphosphatidylethanolamine (AAPE). A "non-ether phospholipid" is a phospholipid that does not have an ether bond at position 1 of the glycerol backbone.

As used herein, the term "omega-3 fatty acid" refers to polyunsaturated fatty acids that have the final double bond in the hydrocarbon chain between the third and fourth carbon atoms from the methyl end of the molecule. Non-limiting examples of omega-3 fatty acids include, 5,8,11,14,17-eicosapentaenoic acid (EPA), 4,7,10,13,16,19-docosahexanoic acid (DHA) and 7,10,13,16,19-docosapentanoic acid (DPA).

As used herein, the terms "triacylglycerid" "triglyceride" and "triacyfgiycerol" and "TAG" refer to is an ester derived from glycerol and three fatty acids, wherein "fatty acid" refers to a carboxylic acid with a long unbranched aliphatic tail (chain), which is either saturated or unsaturated. Palmitic acid is one, non-limiting example of a triacylglyceride.

As used herein, the terms "% w/w (weight/weight)" and "w/w %" and grammatical equivalents refer to the amount (percent) of a given substance in a composition on weight: weight basis. For example, a composition comprising 50% w/w phospholipids means that the mass of the phospholipids is 50% of the total mass of the composition (i.e., 50 grams of phospholipids in 100 grams of the composition, such as an oil).

As used herein the term "algae" refers to a unicellular or multicellular organism formerly classified as plants, occurring in fresh or salt water, autotrophic or heterotrophic, but that lack true stems, roots, and leaves. As used herein the term "heterotrophic" refers to an organism that cannot synthesize its own food and is dependent on organic substances (e.g., complex and/or simple organic substances) for nutrition. Thus, the term "heterotrophic algae" refer to an algae that cannot synthesize its own food and is dependent on organic substances for nutrition. As used herein, the term "autotrophic" refers to an organism capable of synthesizing its own food from inorganic substances, using light or chemical energy. The use of the term "algal" also relates to microalgae and thus encompasses the meaning of "microalgal." The term "algal composition" refers to any composition that comprises algae, such as an aquatic composition, and is not limited to the body of water or the culture in which the algae are cultivated. An algal composition can be an algal culture, algal biomass, a concentrated algal culture, or a dewatered mass of algae, and can be in a liquid, semi-solid, or solid form. A non-liquid algal composition can be described in terms of moisture level or percentage weight of the solids. An "algal culture" is an algal composition that comprises live algae. The term "algae" includes macroalgae (commonly known as seaweed) and microalgae.

As used herein, the terms "algal biomass" or "biomass" refers to a collection or mass of algal cells grown in a given area or ecosystem at a given time. The area or ecosystem may be a naturally occurring environment (e.g., body of water) or a synthetic environment (e.g., in a fermentor or bioreactor (e.g., open or closed)).

As used herein, the term "total fat" refers to the sum of triglycerides, phospholipids, wax ester, and sterols present in a material. For example, "total fat" content of an algal biomass refers to the sum of triglycerides, phospholipids, wax ester, and sterols present in the biomass. In addition, total fat includes both saturated and unsaturated fats.

As used herein, the term "preservative" refers to an agent that extends the storage life of food and non-food products by retarding or preventing deterioration of flavor, odor, color, texture, appearance, nutritive value, or safety. A preservative need not provide a lethal, irreversible action resulting in partial or complete microbial cell destruction or incapacitation. Sterilants, sanitizers, disinfectants, sporicides, virucides and tuberculocidal agents provide such an irreversible mode of action, sometimes referred to as "bactericidal" action. In contrast, a preservative can provide an inhibitory or bacteriostatic action that is reversible, in that the target microbes can resume multiplication if the preservative is removed. The principal differences between a preservative and a sanitizer primarily involve mode of action (a preservative prevents growth rather than killing microorganisms) and exposure time (a preservative has days to months to act whereas a sanitizer has at most a few minutes to act).

As used herein, the term "yeast" and "yeast cells" refers to eukaryotic microorganisms classified in the kingdom Fungi, having a cell wall, cell membrane and intracellular components. Yeasts do not form a specific taxonomic or phylogenetic grouping. Currently about 1,500 species are known; it is estimated that only 1% of all yeast species have been described. The term "yeast" is often taken as a synonym for S. cerevisiae, but the phylogenetic diversity of yeasts is shown by their placement in both divisions Ascomyeota and Basidiomycota. The budding yeasts ("true yeasts") are classified in the order Saccharomycetales. Most species of yeast reproduce asexually by budding, although some reproduce by binary fission. Yeasts are unicellular, although some species become multicellular through the formation of a string of connected budding cells known as pseudohyphae, or false hyphae. Yeast size can vary greatly depending on the species, typically measuring 3-4 μm in diameter, although some yeast can reach over 40 μm.

As used herein, the terms "selenium-enriched yeast" and "selenized yeast" refer to any yeast (e.g., *Saccharomyces cerevisiae*) that is cultivated in a medium containing inorganic selenium salts. The present invention is not limited by the selenium salt used. Indeed, a variety of selenium salts are contemplated to be useful in the present invention including, but not limited to, sodium selenite, sodium selenate, cobalt selenite or cobalt selenate. Free selenomethionine (e.g., not associated with a cell or yeast) can also be used as the selenium source for selenium enriched yeast as yeast does incorporate this form of selenium. During cultivation, because of the chemical similarity between selenium and sulfur, yeast incorporate selenium in place of sulfur in what are normally sulfur-containing organic compounds within the cell. A selenium-containing compound in such yeast preparations is selenomethionine which will be present in a form that is incorporated into polypeptides/proteins. The amount of total cellular selenium present in the form of selenomethionine in such preparations will vary, but can be between 10 and 100%, 20-60%, 50-75% and between 60 and 75%. The remainder of the organic selenium in selenized yeast preparations is predominantly made up of intermediates in the pathway for selenomethionine biosynthesis. These include, but are not limited to, selenocysteine, selenocystathionine, selenohoinocysteine and seleno-adenosylsetenomethionine. The amount of residual inorganic selenium salt in the finished product is generally quite low ($\leq 2\%$). However, the present invention is not limited by this percentage, as preparations that contain more (e.g., between 2 and 70%) or less (e.g., between 0.1 and 2%) than this percentage are also encompassed by the invention.

As used herein, the term "SEL-PLEX" refers to a dried, nonviable selenium-enriched yeast (e.g., *Saccharomyces cerevisiae* of accession number CNCM I-3060, Collection Nationale De Cultures De Microorganismes (CNCM), Institut Pasteur, Paris, France) cultivated in a fed-batch fermentation that provides incremental amounts of cane molasses and selenium salts in a manner that minimizes the detrimental effects of selenium salts on the growth rate of the yeast and allows for optimal incorporation of inorganic selenium into cellular organic material. Residual inorganic selenium is eliminated (e.g., using a rigorous washing process) and does not exceed 2% of the total selenium content.

As used herein, the term "organic selenium" refers to any organic compound wherein selenium replaces sulfur. Thus, organic selenium can refer to any such compound biosynthesized by yeast, or it can refer to free organic selenocompounds that are chemically synthesized. An example of the latter is free selenomethionine.

As used herein, the term "inorganic selenium" generally refers to any selenium salt (e.g., sodium selenite, sodium selenate, cobalt selenite and cobalt selenate). There are also a variety of other inorganic selenium sources (See e.g., those listed in the Merck index). Selenized yeast may be generated using a source of inorganic selenium including, but not limited to, sodium selenite, sodium selenate, cobalt selenite, cobalt selenate, selenic acid, selenious acid, selenium bromide, selenium chloride, selenium hexafluoride, selenium oxide, selenium oxybromide, selenium oxychloride, selenium oxyfluoride, selenium sulfides, selenium tetrabromide, selenium tetrachloride and selenium tetrafluoride.

As used herein, the term "yeast cell wall" also referred to as "YCW" refers to the cell wall of a yeast organism that surrounds the plasma membrane and the intracellular components of the yeast. Yeast cell wall includes both the outer layer (mainly mannan) and the inner layer (mainly glucan and chitin) of the yeast cell wall. A function of the cell wall is to provide structure and protect the metabolically active cytoplasm. Signaling and recognition pathways take place in the yeast cell wall. The composition of yeast cell wall varies from strain to strain and according to growth conditions of yeast.

As used herein, the term "purified" or "to purify" refers to the removal of components from a sample. For example, yeast cell walls or yeast cell wall extracts are purified by removal of non-yeast cell wall components (e.g., plasma membrane and/or yeast intracellular components); they are also purified by the removal of contaminants or other agents other than yeast cell wall. The removal of non-yeast cell wall components and/or non-yeast cell wall contaminants results in an increase in the percent of yeast cell wall or components thereof in a sample.

As used herein, the term "in vivo" refers to studies and/or experiments conducted within a living organism, occurring within a biological organism.

As used herein, the term "in vitro" refers to an artificial environment outside the living organism and to biological processes or reactions that would normally occur within an organism but are made to occur in an artificial environment. In vitro environments can comprise, but are not limited to, test tubes and cell culture.

As used herein, the term "high-performance liquid chromatography" and the term "HPLC" refer to a form of liquid chromatography to separate compounds. The compounds are dissolved in solution. Compounds are separated by injecting a plug of the sample mixture onto the column. HPLC instruments comprise a reservoir of mobile phase, a pump, an injector, a separation column, and a detector. The presence of analytes in the column effluent is recorded by quantitatively detecting a change in refractive index, UV-VIS absorption at a set wavelength, fluorescence after excitation with a suitable wavelength, or electrochemical response.

As used herein, the term "scanning electron microscopy" and the term "SEM" refer to use of a type of electron microscope that images the sample surface by scanning it with a high-energy beam of electrons in a raster scan pattern. The electrons interact with the atoms that make up the sample producing signals that contain information about the sample's surface topography, composition and other properties such as electrical conductivity.

As used herein, the term "fixation agent" refers to a chemical that is capable of fixing one substance to another in order to "fix", stabilize, or otherwise preserve the substance in its current form to prevent the substance from degrading or otherwise changing. Often, fixation agents are used in scanning electron microscopy (SEM) to prepare the sample. Primary fixation agent: as used herein, the terms "primary fixation agent" refers to the first fixation agent used to "fix" a substance. Secondary fixation agent: as used herein, the terms "secondary fixation agent" refers to the second fixation agent used to "fix" a substance. Tertiary fixation agent: as used herein, the terms "tertiary fixation agent" refers to the third fixation agent used to "fix" a substance.

As used herein, the term "analyte" refers to an atom, a molecule, a grouping of atoms and/or molecules, a substance, or chemical constituent. An analyte, in and of itself cannot be measured; rather, aspects or properties (physical, chemical, biological, etc.) of the analyte can be determined using an analytical procedure, such as HPLC. For example, one cannot measure a "chair" (analyte-component) in and of itself, but, the height, width, etc. of a chair can be measured.

Likewise, one cannot measure a mycotoxin but can measure the mycotoxin fluorescence that is related to its concentration.

As used herein, the term "signal" is used generally in reference to any detectable process that indicates that a reaction has occurred (for example, binding of antibody to antigen). Signals can be assessed qualitatively as well as quantitatively. Examples of types of "signals" include, but are not limited to, radioactive signals, fluorimetric signals or colorimetric product/reagent signals.

As used herein, the term "bioavailability" refers to the fraction of a molecule or component that is available to an organism or reaches the systemic circulation. When a molecule or component is administered intravenously, its bioavailability is 100%. However, when a molecule or component is administered via other routes (such as orally), its bioavailability decreases (due to incomplete absorption and first-pass metabolism). In a nutritional setting, bioavailability refers to the rates of absorption and utilization of a nutrient. Different forms of the same nutrient, for example, may have different bioavailabilities.

As used herein, the term "effective amount" refers to the amount of a composition sufficient to effect beneficial or desired results. An effective amount can be administered and/or combined with another material in one or more administrations, applications or dosages and is not intended to be limited to a particular formulation or administration route.

As used herein, the term "digest" refers to the conversion of food, feedstuff's, or other organic compounds into absorbable form; to soften, decompose, or break down by heat and moisture or chemical action.

As used herein, "digestive system" refers to a system (including gastrointestinal system) in which digestion can or does occur.

As used herein, the term "feedstuffs" refers to material(s) that are consumed by mammals (e.g., humans and animals) and contribute energy and/or nutrients to a mammal's diet. Examples of feedstuffs include, but are not limited to, Total Mixed Ration (TMR), forage(s), pellet(s), concentrate(s), premix(es) coproduct(s), grain(s), distiller grain(s), molasses, fiber(s), fodder(s), grass(es), hay, kernel(s), leaves, meal, soluble(s), and supplement(s).

As used herein, the terms "food supplement" "dietary supplement" "dietary supplement composition" and the like refer to a food product formulated as a dietary or nutritional supplement to be used as part of a diet. Exemplary dietary supplement compositions are described herein.

As used herein, the term "animal" refers to those of kingdom Animalia. This includes, but is not limited to livestock, farm animals, domestic animals, pet animals, marine and freshwater animals, and wild animals.

As used herein, the terms "administration" and the term "administering" refer to the act of giving a substance, including a drug, prodrug, or other agent, or therapeutic treatment to a subject (e.g., a subject or in vivo, in vitro, or ex vivo cells, tissues, and organs). Exemplary routes of administration can be through the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the term "co-administration" and the term "co-administering" refer to the administration of at least two agent(s) or therapies to a subject and/or material (e.g., feedstuff). Co-administration of two or more agents or therapies can be concurrent, or a first agent/therapy can be administered prior to a second agent/therapy.

As used herein, the term "treatment" refers to measures taken that facilitate the improvement and/or reversal of the symptoms of disease. The term "treatment" refers to both therapeutic treatment and prophylactic or preventative measures. For example, subjects that may benefit from treatment with compositions and methods of the present invention include those already with a disease and/or disorder as well as those in which a disease and/or disorder is to be prevented (e.g., using a prophylactic treatment of the present invention).

As used herein, the term "at risk for disease" refers to a subject that is predisposed to experiencing a particular disease. This predisposition may be genetic (e.g., a particular genetic tendency to experience the disease, such as heritable disorders), or due to other factors (e.g., age, weight, environmental conditions, exposures to detrimental compounds present in the environment, etc.).

As used herein, the term "disease", the term "infection" and the term "pathological condition or response" refer to a state, signs, and/or symptoms that are associated with an impairment of the normal state of a living animal or of any of its organs or tissues that interrupts or modifies the performance of normal functions, and may be a response to environmental factors (such as malnutrition, industrial hazards, or climate, including mycotoxicosis), specific infective agents (such as worms, bacteria, or viruses), to inherent defect of the organism (such as various genetic anomalies), or combinations of these and other factors.

As used herein, the term "suffering from disease" refers to a subject (e.g., an animal or human subject) that is experiencing a particular disease and is not limited to any particular signs or symptoms, or disease.

As used herein, the term "toxic" refers to any detrimental, deleterious, harmful, or otherwise negative effect(s) on a subject, a cell, or a tissue as compared to the same cell or tissue prior to the contact or administration of the toxin/toxicant.

As used herein, the term "pharmaceutical composition" refers to the combination of an active agent with a carrier, inert or active, making the composition especially suitable for diagnostic or therapeutic use in vitro, in vivo or ex vivo.

As used herein, the term "pharmaceutically acceptable" and the term "pharmacologically acceptable" refer to compositions that do not substantially produce more known adverse reactions than known beneficial reactions.

As used herein, the term "inoculation" refers to the act of introducing a microorganism or suspension of microorganisms (e.g., algae, yeast, fungi, bacteria, etc.) into a culture medium. Inoculation is the act or process of introducing something into an environment in which it will grow or reproduce.

As used herein, the term "inoculum" and the term "pre-inoculum" refer to cells used in an inoculation, such as cells added to start a culture.

As used herein, the term "centrifugation" refers to the separating of molecules by size or density using centrifugal forces generated by a spinning rotor that puts an object in rotation around a fixed axis, applying a force perpendicular to the axis. The centrifuge works using the sedimentation principle, where the centripetal acceleration is used to evenly distribute substances of greater and lesser density into different layers of density.

As used herein, the term "concentration" refers to the amount of a substance per defined space. Concentration usually is expressed in terms of mass per unit of volume. To dilute a solution, one must add more solvent, or reduce the amount of solute (e.g., by selective evaporation, spray drying, freeze drying, e.g., concentrated yeast cell wall extract or concentrated modified yeast cell wall extract). By contrast, to concentrate a solution, one must add more solute, or reduce the amount of solvent.

As used herein, the term "layer" refers to a usually horizontal deposit organized in stratum of a material forming an overlying part or segment obtained after separation by centrifugation in relation with the density properties of the material.

As used herein, the term "harvest" refers to the act of collecting or bringing together materials that have been produced (e.g. bringing together materials produced during yeast production).

As used herein, the term "drying" refers to spray drying, freeze drying, air drying, vacuum drying or any other kind of process that reduces or eliminates liquid in a substance.

As used herein, the term "spray drying" refers to a commonly used method of drying a substance containing liquid using hot gas to evaporate the liquid to reduce or eliminate liquid in the substance. In other words the material is dried by way of spraying or atomizing into a draft of heated dry air.

As used herein, the term "freeze-drying" and the term "lyophilization" and the term "cryodesiccation" refer to the removal of a solvent from matter in a frozen state by sublimation. This is accomplished by freezing the material to be dried below its eutectic point and then providing the latent heat of sublimation. Precise control of heat input permits drying from the frozen state without product meltback. In practical application, the process is accelerated and precisely controlled under reduced pressure conditions.

As used herein, the term "dry free flowing powder" refers to a free flowing dry powder, e.g. a powder that can be poured from a container, bag, vessel etc without hindrance of large clumps.

As used herein, the term "grinding" refers to reducing particle size by impact, shearing, or attrition.

As used herein, the term "sample" is used in a broad sense including a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples.

DETAILED DESCRIPTION OF THE INVENTION

This invention relates to compositions comprising high lipid content algae and methods of making and utilizing the same. In particular, the invention relates to high lipid content algae biomass and algal lipid materials derived from the same, methods of making the same, as well as to biofuels (e.g., biodiesel) and dietary compositions (e.g., animal feeds) comprising or made from the same. Compositions and methods of the invention find use in a variety of applications including biofuel, dietary (e.g., human and animal nutrition), therapeutic as well as research applications.

Accordingly, in one aspect of the invention, there is provided a process for the preparation of an algal biomass containing elevated amounts (e.g., on a w/w basis) of total fat. For examples, as described herein, in some embodiments, the invention provides a method of generating an algal biomass containing a desired, high level of total fat content (e.g., greater than 60% total fat, in contrast to conventional methods that generate algal biomass containing a significantly lower level of total fat content (e.g., 60% or less total fat)). A great challenge of algal-based biofuel (e.g., biodiesel) is to ensure that the biomass is not made at the expense of more energy than is obtained in the final fuel product. Accordingly, in some embodiments, the invention provides a method of generating an algal biomass containing greater than 65% total fat. In some embodiments, the invention provides a method of generating an algal biomass containing greater than 66% total fat. In some embodiments, the invention provides a method of generating an algal biomass containing greater than 67% total fat. In some embodiments, the invention provides a method of generating an algal biomass containing greater than 68% total fat. In some embodiments, the invention provides a method of generating an algal biomass containing greater than 69% total fat. In some embodiments, the invention provides a method of generating an algal biomass containing greater than 70% total fat. In some embodiments, the invention provides a method of generating an algal biomass containing greater than 70% (e.g., greater than 71, 72, 73, 74, 75, 76, 77, 78, 79, 80, 81, 82, 83, 84, 85, 86, 87, 88, 89, 90% or more) total fat on a w/w basis. In some embodiments, the method utilizes a closed bioreactor system (e.g., a fermentor), although the invention is not so limited (e.g., in some embodiments, open bioreactors may be utilized). In a preferred embodiment, growth of an algal biomass of the invention is conducted under aseptic conditions. In another preferred embodiment, algae are grown (e.g., to generate an algal biomass containing a high fat content (e.g., greater than 67% fat)) in a fed-batch process.

In some embodiments, the invention provides a method of culturing algae to produce an algal biomass comprising a desired, high total fat content (e.g., 67% or more total fat) as described in Examples 1 and 2. For example, in some embodiments, the invention provides a method of culturing algae comprising culturing the algae in a stepwise manner so as to produce an algal biomass comprising a desired, high total fat content (e.g., 67% or more total fat). In some embodiments, a stepwise process for culturing algae comprises thawing a stored strain of algae and adding (e.g., aseptically) the thawed algae to a 1 L shake flask contain medium comprising a carbon source (e.g., sugar (e.g., glucose)), yeast extract and sea salt. In some embodiments, the carbon source is present in a concentration of 50 g/L, the yeast extract is present in a concentration of 10 g/L and/or the sea salt is present in a concentration of 4 g/L. In some embodiments, the 1 L shake flask containing algae and medium are maintained at 30 C and shaken (e.g., at about 100-400 RPM) until such time that the algae have entered exponential growth phase but have not fully depleted the carbon source (e.g., sugar (e.g., glucose)). Experiments conducted during development of embodiments of the invention have determined that the algae enter exponential growth but do not fully deplete the carbon source (e.g., sugar (e.g., glucose)) at a time period between 72-144 hours. Thus, in some embodiments, algae cultivated in a 1 L culture flask at 30 C for 72-144 hours at about 100-400 RPM (e.g., 250 RPM) in medium comprising a carbon source (e.g., sugar (e.g., glucose)), yeast extract and sea salt is used to inoculate a first seed stage culture (e.g., in a larger vessel (e.g., 40, 27 or 18 L vessel)). In some embodiments, the culture medium used in a first seed stage comprises a carbon source (e.g., sugar (e.g., glucose)), yeast extract, magnesium sulfate, calcium chloride and/or magnesium chloride. In a preferred embodiment, the culture medium used in a first seed stage comprises about 50 g/L of a carbon source (e.g., sugar (e.g., glucose)), about 7.5 g/L yeast extract, about 0.15 g/L magnesium sulfate, about 0.15 g/L calcium chloride and/or 0.15 g/L magnesium chloride. In some embodiments, the first seed stage culture is run at 30 C under airflow and agitation conditions so as to maintain dissolved oxygen at about 7-15% (e.g., 8, 9, 10, 11, 12, 13, 14%), although lower and higher dissolved oxygen conditions may be utilized. In a preferred embodiment, the first seed stage culture is run at 30 C under airflow and agitation conditions so as to maintain dissolved oxygen at about 10%. In some embodiments, the first seed stage culture containing algae and medium are maintained at 30 C and cultivated until such time that the algae have entered exponential growth phase and at least 20 g/L of carbon source (e.g., sugar (e.g., glucose)) has been consumed but the carbon source has not been fully depleted. Experiments conducted during development of embodiments of the invention determined that the algae enter exponential growth, consume at least 20 g/L of carbon source (e.g., sugar (e.g., glucose)) but do not fully deplete the carbon source (e.g., sugar (e.g., glucose)) at a time period between 24-48 hours after inoculation of the first seed stage culture. In some embodiments, algae cultivated in first seed stage culture at 30 C for 24-48 hours in medium comprising a carbon source (e.g., sugar (e.g., glucose)), yeast extract, magnesium sulfate, calcium chloride and magnesium chloride are used to inoculate a second seed stage culture in yet a larger vessel (e.g., 2000 L vessel). In some embodiments, the culture medium used in a second seed stage culture comprises a carbon source (e.g., sugar (e.g., glucose)), yeast extract, magnesium sulfate, calcium chloride and/or magnesium chloride. In a preferred embodiment, the culture medium used in a second seed stage culture comprises about 50 g/L of a carbon source (e.g., sugar (e.g., glucose)), about 7.5 g/L yeast extract, about 0.15 g/L magnesium sulfate, about 0.15 g/L calcium chloride and/or 0.15 g/L magnesium chloride. In some embodiments, the second seed stage culture is run at 30 C under airflow and agitation conditions so as to maintain dissolved oxygen at about 7-15% (e.g., 8, 9, 10, 11, 12, 13, 14%), although lower and higher dissolved oxygen conditions may be utilized. In a preferred embodiment, the second seed stage culture is run at 30 C under airflow and agitation conditions so as to maintain dissolved oxygen at about 10%. In some embodiments, the second seed stage culture containing algae and medium are maintained at 30 C and cultivated until such time that the algae have entered exponential growth phase, and at least 20 g/L of carbon source (e.g., sugar (e.g., glucose)) has been consumed, but the carbon source has not been fully depleted. Experiments conducted during development of embodiments of the invention determined that the algae enter exponential growth, consume at least 20 g/L of carbon source (e.g., sugar (e.g., glucose)) but do not fully deplete the carbon source (e.g., sugar (e.g., glucose)) at a time period between 24-48 hours after inoculation of the second seed stage culture. In some embodiments, algae cultivated in second seed stage culture at 30 C for 24-48 hours in medium comprising a carbon source (e.g., sugar (e.g., glucose)), yeast extract, magnesium sulfate, calcium chloride and magnesium chloride are used to inoculate a large scale vessel (e.g., 70,000 L, 120,000 L, 220,000 L or larger vessel (e.g., a main fermentor)) containing medium used for further culturing/fermentation of the algae. In some embodiments, upon transfer of the second seed stage culture to the large scale vessel (e.g., main fermentor), the culture medium (e.g., the batched medium) present in the large scale vessel (e.g., main fermentor) comprises a carbon source (e.g., sugar (e.g., glucose)), yeast extract, magnesium sulfate, urea, calcium chloride, magnesium chloride and/or monopotassium phosphate. In a preferred embodiment, the culture medium used in a large scale (e.g., 70,000 L, 120,000 L, 220,000 L or larger vessel (e.g., main fermentor)) culture comprises about 50 g/L of a carbon source (e.g., sugar (e.g., glucose)), about 7.5 g/L yeast extract, about 4.0 g/L magnesium sulfate, about 1 g/L urea, about 2 g/L calcium chloride, about 2 g/L magnesium chloride and/or about 0.25 g/L monopotassium phosphate. In some embodiments, the large scale culture is run at 30 C under airflow and agitation conditions so as to maintain dissolved oxygen at about 7-15% (e.g., 8, 9, 10, 11, 12, 13, 14%), although lower and higher dissolved oxygen conditions may be utilized. In a preferred embodiment, the large scale culture is run at 30 C under airflow and agitation conditions so as to maintain dissolved oxygen at about 10%. In a preferred embodiment, the carbon source (e.g., sugar (e.g., glucose)) is maintained at 10 g/L for a period of time (e.g., 1 or more days (e.g., 2, 3, 4, 5, 6, 7, 8, 9, 10, 11, 12, 13, 14 or more days (e.g., using a fed-batch process)). For example, in some embodiments, after a desired amount of glucose has been consumed by algae in the large scale vessel (e.g., after about 20-30 g/L of glucose has been consumed by the algae in the large scale vessel (e.g., after 30 g/L of glucose has been consumed)), glucose and fed-batch feeds are started. Experiments conducted during development of embodiments of the invention determined that the fed-batch feeds be added for about 34 hours, although shorter (e.g., about 32, 28, 24, 20 hours or fewer) and longer (e.g., 36, 38, 42, 46, 60, 72, 84, 96, 108, 120, 132, 144, 156, 168 hours or more) time periods may be used. In further preferred embodiments, upon completion of the fed-batch process, cultivation of the algae is continued in the large scale vessels until all nutrients are removed/consumed from the medium. Experiments conducted during development of embodiments of the invention determined that the nutrients are depleted from the medium between about 12 and 2.4 hours after cessation of the fed-batch process. In some embodiments, the algal biomass is harvested from the large scale culture medium/broth and utilized as described herein. In some embodiments, the large scale culture broth is centrifuged to obtain the algal biomass. In some embodiments, the large scale culture broth is cooled prior to centrifugation. Although an understanding of a mechanism is not needed to practice the invention, and the invention is not limited to any particular mechanism of action, in some embodiments, chilling the culture broth increases the density of the algal biomass comprising elevated levels of total fat (e.g., lipids/oil) and allows a larger recovery of the biomass than is achieved in the absence of chilling the culture broth (See, e.g., Example 3). The invention is not limited by the temperature to which the large scale culture is chilled prior to centrifugation. In some embodiments, the large scale culture is chilled to a temperature between 0-50 C, between 5-40 C, 5-25 C, 5-15 C or 5-10 C.

Thus, the invention utilizes both batch and fed-batch modes of culturing algae (e.g., alone and/or subsequent to a first and/or second seed stage) in order to generate an algal biomass that contains a desired fat content (e.g., a fat content greater than 67%). The invention is not limited by the individual components present in the media used in either the batch or fed-batch modes. In some embodiments, culture media present at the time of inoculation of a main fermentor (e.g., 70,000 L, 120,000 L, 220,000 L vessel) contains medium with an initial ratio of nitrogen (N):phosphorus (P):potassium (K) of 46:13:8.5. In a preferred embodiment, the N:P:K ratio is the same in the batch and fed-batch culture modes. In some embodiments, the ratio of magnesium (Mg):calcium (Ca) is 3:1 in culture media used in both batch and fed-batch modes. In another embodiment, the ratio of chloride (Cl2):sulfate (SO4)) is 1:1 in culture media used in both batch and fed-batch modes. In some embodiments, the ratio of sulfate (SO4):phosphate (PCM) in media at the time of inoculation of a main fermentor (e.g., 70,000 L, 120,000 L, 220,000 L vessel) is 16:1. In some embodiments, the total ratio of sulfate (SO4):phosphate (PO4) that has been batched and fed at the end of a full culture (e.g., including inoculum, first seed stage, second seed stage and main fermentor cultures) that generates an algal biomass containing a desired fat content (e.g., greater than 67% fat) is 5.3:1. In some embodiments, the ratio of chloride (Cl2):phosphate (PCM) in media at the time of inoculation of a main fermentor (e.g., 70,000 L, 120,000 L, 220,000 L vessel) is 16:1. In some embodiments, the total ratio of chloride (Cl2):phosphate (PCM) that has been batched and fed at the end of a full culture (e.g., including inoculum, first seed stage, second seed stage and main fermentor cultures) that generates an algal biomass containing a desired fat content (e.g., greater than 67% fat) is 5.3:1.

As described in Example 2 below, the invention also provides a composition comprising an algal biomass (e.g., a dried algal biomass (e.g., generated according to a method described herein)) containing a desired amount of total fat and/or other components. For example, in some embodiments, the invention provides an algal biomass (e.g., a dried biomass) containing greater than 67% total fat (e.g., greater than about 68% total fat, greater than about 69% total fat, greater than about 70% total fat, greater than about 71% total fat, greater than about 72% total fat, greater than about 73% total fat, greater than about 74% total fat, greater than about 75% total fat, greater than about 76% total fat, greater than about 77% total fat, greater than about 78% total fat or higher amount of total fat). In some embodiments, an algal biomass (e.g., containing greater than 67% total fat) is dried such that the biomass contains less than 5% moisture (e.g., less than 4.5% moisture, less than 4% moisture, less than 3.5% moisture, less than 3% moisture, less than 2.5% moisture, less than 2% moisture, or less than 1.5% moisture). In some embodiments, an algal biomass of the invention (e.g., a dried biomass containing less than 5% moisture) contains about 170-250 mg/g or more docosahexaenoic acid (DHA) (e.g., about 170-180 mg/g DHA, about 180-190 mg/g DHA, about 190-200 mg/g DHA, about 200-210 mg/g DHA, about 210-220 mg/g DHA, about 220-230 mg/g DHA, about 230-240 mg/g DHA, about 240-250 mg/g DHA, or more than 250 mg/g DHA). In some embodiments, an algal biomass of the invention (e.g., a dried biomass containing less than 5% moisture) contains about 150-400 mg/g or more palmitic acid (IUPAC name: hexadecanoic acid (e.g., about 150-200 mg/g, about 200-225 mg/g, about 225-250 mg/g, about 250-275 mg/g, about 275-300 mg/g, about 300-325 mg/g, about 325-350 mg/g, about 350-375 mg/g, about 375-400 mg/g, or more than 400 mg/g)). In some embodiments, an algal biomass of the invention (e.g., a dried biomass containing less than 5% moisture) contains about 300-600 mg/g or more total fatty acids (e.g., about 300-350 mg/g, about 350-400 mg/g, about 400-450 mg/g, about 450-500 mg/g, about 500-550 mg/g, about 550-600 mg/g, or more than 600 mg/g fatty acids)). In some embodiments, an algal biomass of the invention (e.g., a dried biomass containing less than 5% moisture) contains less than about 15% protein (e.g., less than about 14% protein, less than about 13% protein, less than about 12% protein, less than about 11% protein, less than about 10% protein, less than about 9% protein, or less than about 8% protein).

The invention is not limited by the strain or species of algae utilized in the methods and compositions described herein. Indeed, a variety of algae find use in the invention including, but not limited to, one or more species of the genus *Thraustochytrium*. In some embodiments, the algae is a species of the genus *Chlorella*. In some embodiments, the algae is a species of the genus *Schizochytrium*. In some embodiments, the algae is a species of the genus *Crypthecodinium*. In some embodiments, the algae is *Thraustochytrium striatum, Thraustochytrium roseum, Thraustochytrium aureum, Crypthecodinium cohnii,* and/or *Aurantiochytrium* sp. In a preferred embodiment, *Schizochytrium limacinum* is utilized in the methods and compositions described herein. The invention is not limited by the type of lipids produced by a process to generate an algal biomass with elevated levels of lipids disclosed herein. In some embodiments, the lipids generated by a process of the invention include, but are not limited to, myristic acid, palmitic acid, oleic acid, linoleic acid, docosapentaenoic acid (DPA), docosahexaenoic acid (DHA), and stearic acid. These lipids have been useful for both animal and human health, for prevention of various diseases such as cardiovascular and inflammatory diseases and in infant nutrition for proper brain development and retinal vision in children.

In another embodiment, the invention provides a process for production of an algal biomass containing elevated levels (e.g., greater than 67%) of total fat from an algae species (e.g., *Schizochytrium limacinum*), wherein the process comprises culturing algae in a first feed batch vessel comprising medium (e.g., comprising about 50 g/L of a carbon source (e.g., sugar (e.g., glucose)), about 7.5 g/L yeast extract, about 0.15 g/L magnesium sulfate, about 0.15 g/L calcium chloride and/or 0.15 g/L magnesium chloride), transferring (e.g., aseptically) the first feed batch culture to a second seed batch culture medium(e.g., comprising about 50 g/L of a carbon source (e.g., sugar (e.g., glucose)), about 7.5 g/L yeast extract, about 0.15 g/L magnesium sulfate, about 0.15 g/L calcium chloride and/or 0.15 g/L magnesium chloride), transferring (e.g., aseptically) the second seed batch culture to a large scale culture vessel containing medium (e.g., a main fermentor (e.g., 70,000 L, 120,000 L, 220,000 L vessel, containing, for example, medium comprising about 50 g/L of a carbon source (e.g., sugar (e.g., glucose)), about 7.5 g/L yeast extract, about 4.0 g/L magnesium sulfate, about 1 g/L urea, about 2 g/L calcium chloride, about 2 g/L magnesium chloride and/or about 0.25 g/L monopotassium phosphate), wherein the glucose level of the large scale culture vessel is maintained at 10 g/L using a fed-batch process, wherein the algal cells are harvested from the large scale culture between 12-24 hours after cessation of the fed-batch process after all of the nutrients have been removed/consumed from the medium.

Another embodiment of the invention provides a process for production of an algal biomass containing elevated levels (e.g., greater than 67%) of total fat from an algae species (e.g., *Schizochytrium limacinum*), wherein the culture medium (e.g., during each stage of fermentation (e.g., first seed stage, second seed stage and/or batch culture (fed-batch) cultivation stage)) comprises a carbon source (e.g., a sugar), yeast extract, a phosphate source (e.g., monopotassium phosphate, magnesium sulfate and/or zinc sulfate), a nitrogen source (e.g., urea), magnesium chloride, and/or calcium chloride. In a preferred embodiment, the invention provides a process for production of an algal biomass containing elevated levels (e.g., greater than 67%) of total fat from a strain of algae wherein the culture medium (e.g., during each stage of fermentation (e.g., first seed stage, second seed stage and/or batch culture (fed-batch) cultivation stage)) comprises sugar, yeast extract, monopotassium phosphate, magnesium sulfate, zinc sulfate), urea, magnesium chloride, and/or calcium chloride. However, the invention is not limited by the type of nutrient utilized in a culture medium in which algae are grown. In some embodiments, one or more carbon sources are added to the medium. Examples of carbon sources include, but are not limited to, carbohydrates such as glucose, fructose, xylose, saccharose, maltose or soluble starch as well as oleic acid, fats such as soybean oil, molasses, glycerol, mannitol, and sodium acetate, cotton seed flour, glycerol, molasses and corn steep liquor. In some embodiments, one or more nitrogen sources are added to the medium. Examples of nitrogen sources include, but are not limited to, natural nitrogen sources such as peptone, yeast extract, malt extract, meat extract, casamino acid and corn steep liquor, organic nitrogen sources such as sodium glutamate and urea, or inorganic nitrogen sources such as ammonium acetate, ammonium sulfate, ammonium chloride, ammonium nitrate and sodium sulfate. In some embodiments, one or more phosphate sources are added to the medium. Examples of phosphate sources include, but are not limited to, potassium phosphate and potassium dihydrogen phosphate, inorganic salts, such as ammonium sulfate, sodium sulfate, magnesium sulfate, iron sulfate, zinc sulfate, and copper sulfate. In some embodiments, magnesium chloride, calcium chloride, and/or vitamins are included in the culture medium.

The invention is not limited by the amount (e.g., concentration) of each of these components in the culture medium. In some embodiments, an amount is utilized that is not harmful to algal growth. In a preferred embodiment, the amount (e.g., concentration and/or ratio) of each medium ingredient is set at a level (e.g., during each stage of fermentation (e.g., first seed stage, second seed stage and/or batch culture (fed-batch) cultivation stage) that promotes the formation of high fat content algae (e.g., an algal biomass comprising 67% or greater fat content). In some embodiments, the carbon source (e.g., sugar) is present in culture medium at about 20 to 120 grams per liter of medium. In other embodiments, the carbon source (e.g., sugar) is present in culture medium at about 30-70 grams per liter of medium. In still other embodiments, the carbon source (e.g., sugar) is present in culture medium at about 40 to 60 grams per liter of medium. In a preferred embodiment, the carbon source (e.g., sugar) is present in culture medium at about 50 grams per liter of medium. In some embodiments, the ratio of urea to monopotassium phosphate (urea:KH2PO4) is between about 5:0.1 (e.g., about 4.5:0.1; 4:0.25; 3:0.25; 4:0.3; 5:0.3; 5:0.5; 4:0.5; 3:0.5; 2:0.5; or 1:0.5); although higher and lower ratios may be used (e.g., 1:1, 1:2, 1:3 etc.). In a preferred embodiment, the ratio of urea to monopotassium phosphate in culture medium is 4:1. In some embodiments, a culture medium does not contain sodium chloride. In other embodiments, a culture medium contains sodium chloride. In some embodiments, the ratio of magnesium sulfate (MgSO4):calcium chloride (CaCl2) is 1:1. In some embodiments, the ratio of magnesium sulfate (MgSO4):calcium chloride (CaCl2) is 1:2. Indeed, a variety of ratios of magnesium sulfate (MgSO4):calcium chloride (CaCl2) may be used including, but not limited to, 1:1; 1:1.125; 1:1.5; 1:1.75; 1:2; 1:2.125; 1:2.25; 1:2.5; 2.5:1; 2.25:1; 2.125:1; 2:1; 1.75:1; 1.5:1; 1.25:1 or 1.125:1. In a preferred embodiment, the ratio of magnesium sulfate (MgSO4):calcium chloride (CaCl2) in a first seed culture medium is 1:1. In another preferred embodiment, the ratio of magnesium sulfate (MgSO4):calcium chloride (CaCl2) in a second seed culture medium is 1:1. In yet another preferred embodiment, the ratio of magnesium sulfate (MgSO4):calcium chloride (CaCl2) in a large scale culture medium (e.g., main fermentor (e.g., 70,000 L, 120,000 L, 220,000 L vessel) also referred to as a third culture medium herein) is 1:2.

In a further preferred embodiment, after preparing the medium, the pH of the medium need not be adjusted. For example, during a stepwise fermentation process of the invention, the pH of the culture medium in which algae is grown need not be adjusted. Although an understanding of the mechanism is not necessary to practice the invention and the invention is not limited to any particular mechanism of action, in some embodiments, sterile and/or aseptic conditions of the stepwise fermentation process of the invention negates the need to adjust the pH of the culture medium during fermentation. In some embodiments, the pH of the culture medium is between 4.0 and 6.5. Cultivation of the algae during a stepwise fermentation process of the invention may be carried out at a temperature between 10 and 40 C, preferably 17 to 35 C, and most preferably around 30 C. Cultivation may be performed by aeration-agitation culture, shaking culture, stationary culture or the like. In a preferred embodiment, algae are cultured under conditions such that dissolved oxygen is maintained at or slightly above 10%.

In some embodiments, the invention provides a food, feed, nutritional or therapeutic supplement comprising all or a portion of an algal biomass (e.g., a dried algal biomass described herein and/or generated according to the methods and compositions described herein) comprising elevated levels (e.g., greater the 67%) of total fat. For example, in some embodiments, the invention provides a food, feed, nutritional or therapeutic supplement comprising a spray dried algal biomass comprising elevated levels (e.g., greater the 67%) of total fat. In other embodiments, the invention provides a food, feed, nutritional or therapeutic supplement comprising lipids extracted and/or isolated from an algal biomass comprising elevated levels (e.g., greater the 67%) of total fat. The invention is not limited by the type of lipid extracted and/or isolated from an algal biomass comprising elevated levels (e.g., greater the 67%) of total fat. In some embodiments, the lipids comprise myristic acid, palmitic acid, oleic acid, linoleic acid, alpha-linolenic acid (ALA), stearidonic acid (SDA), eicosatrienoic acid, eicosatetraenoic acid, eicosapentaenoic acid (EPA), docosapentaenoic acid (DPA), clupanodonic acid, docosahexaenoic acid (DHA), tetracosapentaenoic acid, and/or tetracosahexaenoic acid. In a preferred embodiment, the lipids comprise DHA and/or palmitic acid.

In some embodiments, the invention provides a process for the preparation of lipids (e.g., those disclosed herein (e.g., docosahexaenoic acid)) comprising: culturing an algae strain (e.g., *Schizochytrium limacinum*) in a first culture medium (e.g., containing 50 g/L of a carbon source (e.g., sugar (e.g., glucose)), 10 g/L yeast extract and 4 g/L sea salt) and incubating the culture at a temperature in the range of 25-35 C for a period of about 72-144 hours; transferring the culture to a second culture medium (e.g., containing 50 g/L of a carbon source (e.g., sugar (e.g., glucose)), about 7.5 g/L yeast extract, about 0.15 g/L magnesium sulfate, about 0.15 g/L calcium chloride and/or 0.15 g/L magnesium chloride) and incubating the culture at a temperature in the range of 25-35 C for a period of about 24-48 hours; transferring the culture to a third culture medium (e.g., containing 50 g/L of a carbon source (e.g., sugar (e.g., glucose)), about 7.5 g/L yeast extract, about 0.15 g/L magnesium sulfate, about 0.15 g/L calcium chloride and/or 0.15 g/L magnesium chloride) and incubating the culture at a temperature in the range of 25-35 C for a period of about 24-48 hours; transferring the culture to a fourth culture medium (e.g., containing 50 g/L of a carbon source (e.g., sugar (e.g., glucose)), about 7.5 g/L yeast extract, about 4.0 g/L magnesium sulfate, about 1 g/L urea, about 2 g/L calcium chloride, about 2 g/L magnesium chloride and/or about 0.25 g/L monopotassium phosphate) and incubating the culture at a temperature in the range of 25-35 C (e.g., 30 C) for a time period of about 24-192 hours (e.g., about 36, about 38, about 42, about 46, about 60, about 72, about 84, about 96, about 108, about 120, about 132, about 144, about 156, about 168, about 180 or about 192 hours); separating the cell biomass from the culture; and extracting lipids from the biomass.

In some embodiments, algae cultures (e.g., grown to produce an algal biomass) are grown in suitable volumes and vessels, ranging from 100 ml to hundreds of thousands of liters, in flasks or large fermentors, using various nutrient media as described herein.

In yet another aspect, the separation of the cell biomass containing lipids is obtained using centrifugation, filtration and/or flocculation or similar techniques. In a preferred embodiment, an algal biomass is obtained from a culture using centrifugation. In a further preferred embodiment, centrifugation occurs after the cell culture is cooled (e.g., to allow recovery of cells containing elevated levels of lipid). In some embodiments, an algal biomass obtained is spray-dried and used (e.g., directly used in animal feeds or for biofuel production).

In one embodiment, the algae is a mixture of different algae species (e.g., one or more of the species of algae described herein). In some embodiments, an algal biomass containing elevated levels of total fat and/or lipids extracted from an algal biomass containing elevated levels of total fat is supplemented with lipids (e.g., polyunsaturated fatty acids) from other sources including, but not limited to, plant sources.

In some embodiments, an algal biomass containing elevated levels of total fat comprise lipids at a concentration (w/w) in a range from about 60-90% (e.g., about 65-90%, about 66-89%, about 67-88%, about 68-87%, about 68-86%, about 69-85%, or about 70-80%). Thus, an algal biomass containing elevated levels of lipids may comprise lipids at a concentration of 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90% and the like. In one embodiment, an algal biomass containing elevated levels of total fat comprise lipids at a concentration of at least 67%.

In some embodiments, DHA is included in an algal biomass composition of the invention in a range from 1% to 75% of total lipids/fatty acids. Thus, the DHA can be provided in the composition in an amount of total fatty acids of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, about 35%, about 40%, about 45%, about 50%, about 55%, about 60%, about 65%, about 70%, about 75%, and the like. In other embodiments, the DHA can be included in a composition in an amount of total fatty acids in a range from 1% to 5%, 1% to 10%, 1% to 15%, 1% to 20%, 1% to 25%, 1% to 30%, 5% to 10%, 5% to 15%, 5% to 20%, 5% to 25%, 5% to 30%, 10% to 15%, 10% to 20%, 10% to 25%, 10% to 30%, 15% to 20%, 15% to 25%, 15% to 30%, 20% to 25%, 20% to 30%, 25% to 30%, 30% to 35%, 35% to 40%, 40% to 45%, 45% to 50%, 50% to 55%, 55% to 60%, 60% to 65%, 65% to 70%, 70% to 75%, and the like.

In some embodiments, palmitic acid is included in an algal biomass composition of the invention in a range from 1% to 75% of total lipids/fatty acids. Thus, the palmitic acid can be provided in the composition in an amount of total fatty acids of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, about 35%, about 40%, about 45%, about 50%, about 55%, about 60%, about 65%, about 70%, about 75%, and the like. In other embodiments, the palmitic acid can be included in a composition in an amount of total fatty acids in a range from 1% to 5%, 1% to 10%, 1% to 15%, 1% to 20%, 1% to 25%, 1% to 30%, 5% to 10%, 5% to 15%, 5% to 20%, 5% to 25%, 5% to 30%, 10% to 15%, 10% to 20%, 10% to 25%, 10% to 30%, 15% to 20%, 15% to 25%, 15% to 30%, 20% to 25%, 20% to 30%, 25% to 30%, 30% to 35%, 35% to 40%, 40% to 45%, 45% to 50%, 50% to 55%, 55% to 60%, 60% to 65%, 65% to 70%, 70% to 75%, and the like.

Additional embodiments of the invention include processes of making animal feed additives. Thus, one aspect of the present invention is a process of making an animal feed additive comprising lipids from an algae (e.g., an algal biomass), the process comprising: cultivating algae to produce a algae biomass containing a desired, elevated level of total fat (e.g., greater than 67% total fat); and extracting algae lipid from the algae biomass to produce a algae oil; and/or removing water from algae biomass to produce a algae biomass with a solids content from about 5% to 100% weight percent; wherein the animal feed additive comprises lipids from the algae. In some embodiments, the fatty acids collected from the algae are short chain, medium or long chain omega-3 fatty acids. In further embodiments, the algae lipid extracted from the algae biomass is combined with a algae biomass with a solids content from about 5% to 100% weight percent.

A feed additive according to the invention can be combined with other food components to produce processed food or feed products (e.g., animal and/or human feed products). Such other food components include one or more enzyme supplements, vitamin food additives and mineral food additives. The resulting (combined) feed additive may be mixed in an appropriate amount with the other food components such as cereal and plant proteins to form a processed food product. Processing of these components into a processed food product can be performed using any conventionally used processing apparatuses. Feed/food additives of the present invention may be used as a supplement in a food/feed by itself, in addition with vitamins, minerals, other feed enzymes, agricultural co-products (e.g., wheat middlings or corn gluten meal), or in a combination therewith.

In a further aspect, the invention provides a process of producing an animal and/or human having an increased tissue content of omega-3 fatty acids, the process comprising feeding to an animal/human a feed additive comprising lipids/fatty acids collected from algae, the feed additive further comprising: (a) an algae lipid extracted from a cultivated algae biomass and/or (b) a algae biomass from a cultivated algae, wherein water is removed from algae biomass to achieve a solids content from about 5 to 100% weight percent, wherein the animal/human displays increased tissue content of omega-3 fatty acids. The invention is not limited to any particular mammal (e.g., animal or human) that may benefit from a composition of the invention. Indeed, animals of the invention include, but are not limited to, any animal whose eggs, meat, milk or other products are consumed by humans or other animals. Thus, animals of the invention include, but are not limited to, fish, poultry (chickens, turkeys, ducks, etc.), pigs, sheep, goats, rabbits, beef and dairy cattle.

In some embodiments, the invention provides a method for treating a mammalian disease in a subject in need thereof by administration to the subject a therapeutically effective amount of a composition of the invention. In some embodiments, a mammalian disease that is treated includes, but is not limited to, a cardiovascular disease, an inflammatory disease, and various cancer diseases. In other embodiments, the cardiovascular diseases to be treated include, but are not limited to, hypertriglyceridemia, coronary heart disease, stroke, acute myocardial infarction and atherosclerosis. In further embodiments, the inflammatory diseases to be treated include, but are not limited to, asthma, arthritis, allergic rhinitis, psoriasis, atopic dermatitis, inflammatory bowel diseases, Crohn's disease, and allergic rhinoconjunctitis. In still further embodiments, the cancer diseases to be treated include, but are not limited to, prostate cancer, breast cancer and colon cancer. In additional embodiments, the mammalian diseases to be treated include psychiatric disorders. Psychiatric disorders include, but are not limited to, depression, bipolar disorder, schizophrenia. In addition, the compositions of the invention can be used to maintain and/or enhance cognitive function.

In some embodiments, the invention provides a method of treating a mammalian disease in a subject in need thereof by administration to the subject a therapeutically effective amount of a lipid composition provided by and/or obtained from an algal biomass containing an elevated level of total fat (e.g., greater than 67% total fat). Subjects that may find benefit from treatment include but are not limited to, avian and mammalian subjects. Mammals of the present invention include, but are not limited to, canines, felines, bovines, caprines, equines, ovines, porcines, rodents (e.g. rats and mice), lagomorphs, primates (including non-human primates), humans, and the like, and mammals in utero. Any mammalian subject in need of being treated according to the present invention is suitable. Mammals of the present invention include, but are not limited to, canines, felines, bovines, caprines, equines, ovines, porcines, rodents (e.g. rats and mice), lagomorphs, primates (including non-human primates), humans, and the like, and mammals in utero. According to some embodiments of the present invention, the mammal is a non-human mammal. In some embodiments, the mammal is a human subject. Mammalian subjects of both genders and at any stage of development (e.g., neonate, infant, juvenile, adolescent, adult) can be treated according to the present invention. Illustrative avians according to the present invention include chickens, ducks, turkeys, geese, quail, pheasant, ratites (e.g., ostrich), domesticated birds (e.g., parrots and canaries), and birds in ovo.

Algae

Any algae capable of producing, using the processes described herein, elevated levels of total fat or algal biomass containing elevated levels of total fat can be used in the processes, compositions, dietary supplements, biofuel and/or biofuel precursor and/or feed additives of the invention. Thus, in some embodiments, the algae of the present invention is selected from *Thraustochytrium, Dinophyceae, Cryptophyceae, Trebouxiophyceae, Pinguiophyceae*, and combinations thereof. In other embodiments, the algae of the invention are selected from *Thraustochytrium striatum, Thraustochytrium roseum, Thraustochytrium aureum, Crypthecodinium cohnii, Parietochloris* spp., *Rhodomonas* spp., *Cryptomonas* spp., *Parietochloris* spp., *Hemisehnis* spp., *Porphyridium* spp., *Glossomastix* spp., and combinations thereof. In further embodiments, the algae of the invention are selected from *Parietochloris incise, Rhodomonas salina, Hemiselmis brunescens, Porphyridium cruentum* and *Glossomastix chrysoplasta*, and combinations thereof. In still further embodiments, the algae of the invention is *Schizochytrium limacinum*.

In some embodiments of the invention, the algae is a mixture of different algae species. In other embodiments, the algae is a single algae species. In some embodiments of the present invention, the algae lipids/fatty acids are provided as an algal oil. In other embodiments, the algae lipids/fatty acids are provided as an algal biomass (e.g., a dried (e.g., powdered) biomass).

Further, the algae of the invention include, but are not limited to, wild-type, mutant (naturally or induced) or genetically engineered algae. In a preferred embodiment, an algae used in the processes, compositions, dietary supplements, biofuel or biofuel precursor and/or feed additives of the invention is a non-genetically modified organism. As used herein, the terms "genetically modified variant," and "genetically modified organism" refer to an algae strain that has a genome which is modified (e.g., mutated, changed) from its normal (e.g., wild-type, naturally occurring) form such that a desired result is achieved.

Additionally, the algae of the invention includes algae having cells with cell walls of reduced thickness as compared to the cells of wild-type algae, whereby the cell wall of reduced thickness improves extractability and/or bioavailability of the algae lipid fraction (e.g., improving the ease of digestibility of the algae and the ease of extractability of the algae lipids/fatty acids from the cells of the algal biomass). Algae having cells with cell walls of reduced thickness as compared to the cells of wild-type algae can be naturally occurring, mutated and/or genetically engineered to have cell walls of reduced thickness as compared to wild-type strains. Thus, in one embodiment of the invention the algae is an algae having a cell wall of reduced thickness as compared to the wild-type algae, whereby the cell wall of reduced thickness improves extractability and/or bioavailability of the algae lipid fraction. Methods of producing algae with reduced cell walls include those found in WO 2006/107736 A1, herein incorporated by reference in its entirety. Thus, the algae can be mutagenized with mutagens known to those of skill in the art including, but not limited to, chemical agents or radiation. In particular embodiments the chemical mutagens include, but are not limited to, ethyl methanesulfonate (EMS), methylmethane sulfonate (MMS), N-ethyl-N-nitrosourea (ENU), triethylmeiamine (TEM), N-methyl-N-nitrosourea (MNU), procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine (MNNG), nitrosoguanidine, 2-aminopurine, 7,12 dimethyl-benz(a)anthracene (DMBA), ethylene oxide, hexamethylphosphoramide, bisulfan, diepoxyalkanes (diepoxyoctane (DEO), diepoxybutane (BEB), and the like), 2-methoxy-6-chloro-9 (3-(ethyl-2-chlor-o-ethylaminopropylamino)acridine dihydrochloride (ICR-170), formaldehyde, and the like. Methods of radiation mutagenesis include, but are not limited to, x-rays, gamma-radiation, ultra-violet light, and the like.

Cell wall mutants can be selected for on the basis of increased sensitivity to detergents or by microscopic observation of alterations in cell wall thickness (See, e.g., WO 2006/107736 A1) or any other method known in the art to detect reduced cell wall thickness or reduced cell wall integrity.

The algae of the invention can be cultured according to techniques described in Examples 1-3.

Accordingly, in some embodiments the algae are cultured at a temperature in a range from 10° C. to 35° C. Thus, the algae can be cultured at a temperature of 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., and the like. In other embodiments, the algae can be grown in ranges from 20° C. to 35° C., although colder (e.g., less than 20° C.) and warmer (e.g., more than 35° C.) may be used. In a preferred embodiment, the algae are grown at about 30° C.

In some embodiments, following cultivation, algae are harvested. In some embodiments, harvesting of algae is performed using conventional procedures known to those of skill in the art including, but not limited to, centrifugation, flocculation or filtration. In a preferred embodiment, prior to harvesting, the algae culture is cooled, thereby allowing algal cells containing elevated levels of total fat to be successfully harvested. The harvested algal cells or algal biomass can then be used directly as a lipid/fatty acid source or extracted to obtain algal oil comprising the lipids/fatty acids. In some embodiments in which the algal biomass is to be used directly, water is removed from the algal biomass to achieve a solids content from about 5 to 100 weight percent. In additional embodiments, an algal biomass that is to be used directly is comprised of algal cells further comprising cell walls that are at least partially disrupted to increase the extractability and/or bioavailability of the algal oil within the cells. The disruption of the algal cells can be carried out according to known techniques including, but not limited to, treating the cells with boiling water or by mechanical breaking such as grinding, pulverizing, sonication, French press, or any other method known to an ordinary artisan.

When the algal biomass is used directly, water is removed from the algal biomass to achieve a solids content from about 5 to 100%. Accordingly, in some embodiments, water is removed from the algal biomass to achieve a solids content of about 5%, 10%, 15%, 20%, 25%, 30%, 35%, 40%, 45%, 50%, 55%, 60%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, and the like. In additional embodiments, water is removed from the algal biomass to achieve a solids content in the range from about 5% to 50%, 5% to 60%, 5% to 70%, 5% to 80%, 5% to 90%, 5% to 95%, 10% to 30%, 10% to 40%, 10% to 50%, 10% to 60% 10% to 65%, 10% to 70%, 10% to 75%, 10% to 80%, 10% to 85%, 10% to 90%, 10% to 95%, 10% to 100%, 15% to 40%, 15% to 50%, 15% to 60%, 15% to 65%, 15% to 70%, 15% to 75%, 15% to 80%, 15% to 85%, 15% to 90%, 15% to 95%, 15% to 100%, 20% to 50%, 20% to 60%, 20% to 65%, 20% to 70%, 20% to 75%, 20% to 80%, 20% to 85%, 20% to 90%, 20% to 95%, 20% to 100%, 25% to 50%, 25% to 60%, 25% to 70%, 25% to 75%, 25% to 80%, 25% to 85%, 25% to 90%, 25% to 95%, 25% to 100%, 30% to 50%, 30% to 60%, 30% to 70%, 30% to 75%, 30% to 80%, 30% to 85%, 30% to 90%, 30% to 95%, 45% to 100%, 50% to 70%, 50% to 75%, 50% to 80%, 50% to 85%, 50% to 90%, 50% to 95%, 50% to 100%, 55% to 75%, 55% to 80%, 55% to 85%, 55% to 90%, 55% to 95%, 55% to 100%, 60% to 75%, 60% to 80%, 60% to 85%, 60% to 90%, 60% to 95%, 60% to 100%, 70% to 80%, 70% to 85%, 70% to 90%, 70% to 95%, 70% to 100%, 75% to 85%, 75% to 90%, 75% to 95%, 75% to 100%, 80% to 85%, 80% to 90%, 80% to 95%, 80% to 100%, 85% to 90%, 85% to 95%, 85% to 100%, 90% to 95%, 95% to 100%, and the like.

In some embodiments, the algal cells of the biomass are disrupted or lysed and the algal lipids extracted. The algal cells can be extracted wet or dry according to conventional techniques to produce a composition containing lipids/fatty acids. The disruption or lysis of the algal cells can be carried out according to conventional techniques including, but not limited to, treating the cells with boiling water or by mechanical breaking such as grinding, pulverizing, sonication, French press, or any other known method. Extraction of the lipids/fatty acids from the lysed cells follow standard procedures used with algal and other organisms that are known including, but not limited to, separating the liquid phase from the solid phase following cell lysis, extracting the lipids/fatty acids in the liquid phase by the addition of a solvent, evaporating the solvent, and recovering the lipids/fatty acids obtained from the liquid phase of the lysed cells.

The invention is not limited to any particular solvent used for extraction. Solvents include, but are not limited to, hexane, chloroform, ethanol, methanol, isopropanol, diethyl ether, dioxan, isopropyl ether, dichloromethane, tetrahydrofuran, petroleum ether and combinations thereof.

In some embodiments, lipids/fatty acids derived from an algal biomass of the invention are provided in the form of free fatty acids, cholesterol esters, salt esters, fatty acid esters, monoglycerides, diglycerides, triglycerides, diacylglycerols, monoglycerols, sphingophospholipids, sphingoglycolipids, or any combination thereof (e.g., for use in processes, compositions, biofuels, food products, dietary supplements, feed additives or other compositions described herein).

Method for Preparing an Algal Biomass

In some embodiments, the invention provides a method for preparing a algal biomass comprising elevated levels of total fat (e.g., greater than 67% lipids), comprising: culturing algae under a culture condition sufficient to provide an algal biomass comprising elevated levels of total fat (e.g., greater than 67% lipids), wherein the algal biomass is harvested at the termination of a logarithmic growth phase of the algae (See, e.g., Examples 1 and 2). As used herein, the term "logarithmic growth phase," refers to a stage of culturing characterized by exponentially increasing numbers of algal cells. Generally, in a culture system, there is a characteristic growth pattern following inoculation that includes a lag phase, an exponential or "logarithmic growth phase," a negative growth acceleration phase, and a plateau or "stationary phase." For example, in the logarithmic growth phase, as growth of the algae continues, cells can reach their maximum rate of cell division and numbers of cells increase in log relationship to time. Within time after the commencement of the log phase, the rate of cell division may begin to decline and some of the cells can begin to die. This is reflected on a growth curve by a gradual flattening out of the line. Eventually the rate of cells dying is essentially equal to the rate of cells dividing, and the total viable population can remain the same for a period of time. This is known as the stationary or plateau phase and is represented on a growth curve as a flattening out of the line where the slope approaches zero. In a preferred embodiment, the algal biomass is cultured under aseptic conditions (e.g., to prevent contamination and/or growth of contaminating microorganisms (e.g., yeast, bacteria, virus, etc.) in the culture).

In some embodiments, the culture condition is sufficient for the algae to produce elevated levels of total fat (e.g., greater than 67% on a w/w basis). The culture conditions comprise a culture medium suitable for growing the algae thereby providing the algae biomass comprising elevated levels of total fat (e.g., greater than 67% on a w/w basis). Suitable culture mediums are described herein. The medium may also comprise salts, vitamins, minerals, metals, and other nutrients. Preferably, the culture condition is sufficient to provide a suitable amount of nutrient and temperature for the algae to grow under conditions that generate an algal biomass comprising elevated levels of total fat.

In some embodiments, culturing comprises limiting a nutrient (e.g., nitrogen, phosphorous) for a suitable time to increase the amount total fat. For example, the culture can be starved of a certain nutrient or transferred to a separate culturing medium lacking a specific nutrient (e.g., phosphorus-free or nitrogen-free medium, or a culture medium containing lower levels of a nutrient). In some embodiments, the culture medium contains an initial content of a nutrient such that that nutrient becomes depleted at a later time during exponential growth but prior to the depletion of other nutrients. In some embodiments, culturing does not comprise limiting a nutrient (e.g., nitrogen, phosphorous) during culture. In some embodiments, culturing of a single algal biomass takes place in two or more types of medium in a sequential manner. In some embodiments, culturing of a single algal biomass takes place in three or more types of medium in a sequential manner. In like manner, culturing of a single algal biomass may take place in two or more vessels, wherein a first vessel is used to inoculate a subsequent vessel, the subsequent vessel is used to inoculate yet another subsequent vessel, and so on. Although an understanding of a mechanism is not needed to practice the invention, and the invention is not limited to any particular mechanism of action, in some embodiments, sequential culturing of a single algal biomass in multiple vessels containing multiple types of medium allows the algal biomass to grow in such a way that the total fat content of the biomass is elevated compared to growth of an algal biomass (e.g., of the same algal species) grown in a single vessel and/or growth medium.

Culturing of the algae can be performed in a conventional bioreactor suitable for culturing the algae to provide an algae biomass. For example, the algae can be cultured by a process including, but not limited to, batch, fed-batch, cell recycle, and continuous fermentation. In a preferred embodiment, the algae are cultured in a fed-batch process.

The invention is not limited to any particular manner or method of harvesting the algae from the culture medium. A variety of methods can be used to harvest the algal cells from the culture medium. In one embodiment, harvesting comprises recovering the algal biomass from the culture medium by separating, for example by filtration (e.g., belt filtration, rotary drum filtration) and/or centrifugation. If desired, the harvested algal cells can then be washed, frozen, lyophilized, spray dried, and/or stored under a non-oxidizing atmosphere of a gas (e.g., $CO_2$, $N_2$) to reduce or eliminate the presence of $O_2$. Optionally, synthetic and/or natural antioxidants including, but not limited to, butylated hydroxytoluene (BHT), butylated hydroxyanisole (BRA), tert-butylhydroquinone (TBHQ), ethoxyquin, beta-carotene, vitamin E, and vitamin C also can be added to the harvested cells.

In some embodiments, the invention provides a method for preparing an algal biomass comprising elevated levels of total fat, the method comprising: culturing algae under a culture condition sufficient to provide an algal biomass comprising elevated levels of total fat and harvesting the algal biomass.

Microalgae Biomass

The invention provides, in some embodiments, an algal biomass and/or a fraction and/or an extract thereof (e.g., for use in biofuel production and/or as a food or feed product).

In some embodiments, the algal biomass comprises an omega-3 fatty acid content of at least 10% dry weight of the biomass, illustratively, about 10% to about 50%, about 10% to about 40%), about 10% to about 30%, about 10% to about 20% dry weight of the biomass. In one embodiment, the algal biomass is prepared in accordance with the methods of the invention. For example, in some embodiments, the algal biomass is prepared by a method comprising: culturing an algae under a culture condition sufficient to provide a algal biomass comprising elevated total fat levels (e.g., greater than 67% w/w), wherein the algal biomass is harvested at a negative growth acceleration phase or a stationary phase. In another embodiment, the algal biomass is harvested from the culture during the exponential, logarithmic growth phase.

Lipid Compositions Prepared from Algal Biomass

In some embodiments, the invention provides a method for preparing a lipid/fatty acid extract (e.g., a lipid/fatty acid composition) from an algal biomass grown under conditions to contain elevated levels of total fat, the method comprising obtaining lipids from an algal biomass cultured under a culture condition sufficient to provide an algal biomass with elevated total fat content (e.g., total fat content greater than 67% of the biomass), wherein the algal biomass is harvested at a negative growth acceleration phase or a stationary phase of the algae. In another embodiment, the algal biomass is harvested during a logarithmic growth phase of the algae.

Methods for obtaining a lipid composition from an algal biomass of the invention include, but are not limited to, extraction, heat, pressure, saponification, sonication, freezing, grinding, ion exchange, chromatography, membrane separation, electrodialysis, reverse osmosis, distillation, chemical derivatization, crystallization, etc. For example, algal lipids can be extracted from the algal cells by any suitable method including, but not limited to, extraction with a solvent including, but not limited to, ethanol, ethyl acetate, isopropyl alcohol, methanol, ethyl acetate, hexane, methylene chloride, methanol, petroleum, chloroform, and the like, or by pressurized liquid hydrocarbons such as butane, pentane, propane, or others (with our without co-solvents), or through supercritical fluid extraction (with or without co-solvents). Optionally, the extracted lipid/fatty acid oil are evaporated under reduced pressure to reduce or remove the solvent and/or produce a sample of concentrated lipid material. In other embodiments, the cells are broken or lysed to obtain the lipid composition, for example into an oil form (e.g., for use as a biofuel or a biofuel precursor). In some embodiments, the extracted oils are subjected to refining. The invention is not limited by the type of refining. In some embodiments, the extracted oils are chemically refined. In some embodiments, the extracted oils are physically refined. In some embodiments, the extracted oils are both chemically and physically refined. Extracted oils (e.g., from an algal biomass grown under conditions to elevate the total fat content of the algal cell (e.g., to above 67%)) may be refined using any conventional refining method. The refining process may remove some or all impurities from the extracted lipids/fatty acids/oils. In some embodiments, the refining process comprises one or more steps to degum, bleach, filter, deodorize and/or polish the extracted lipids/fatty acids/oils.

In some embodiments, the lipids/fatty acids/oils contained in the extracted lipid composition is concentrated by hydrolyzing the lipids to concentrate the lipid fraction by employing a method such as, for example, urea adduction, fractional distillation, column chromatography, and/or supercritical fluid fractionation.

Accordingly, in one embodiment, the step of obtaining a lipid composition from an algal biomass of the invention comprises extracting the lipid composition from the biomass. In another embodiment, the step of obtaining a lipid composition from an algal biomass of the invention comprises contacting the biomass with a polar solvent.

For example, in some embodiments, lipid/fatty acid/oil is extracted from the algal biomass to provide a lipid composition using a solvent under an extraction condition sufficient to extract lipids and/or fatty acids but not sufficient to extract compounds that are insoluble in the solvent. In one embodiment, a lipid/fatty acid composition is extracted from an algal biomass of the invention wherein cellular debris and/or precipitated insoluble compounds are separated from the fraction containing lipid/fatty acid and solvent. In another embodiment, the method further comprises separating the cellular debris and precipitated compounds using a separation method such as filtration, centrifugation, and/or combinations thereof. In some embodiments, the cellular debris and/or precipitated insoluble compounds (e.g., that portion of the algal biomass that are not soluble in a solvent (e.g., proteins, fiber, etc.) are recovered and utilized (e.g., in a food or feed product).

In some embodiments, the solvent is a polar solvent. Examples of polar solvents include, but are not limited to, ethanol, ethyl acetate, isopropyl alcohol, methanol, ethyl acetate, and mixtures thereof. In one embodiment, the polar solvent is ethanol. Extraction of the lipid composition with a solvent can be carried out in a variety of ways. For example, the extraction can be a batch process, a continuous process, or a continuous counter-current process. In a continuous counter-current process, the solvent contact with the microalgae leaches the oil into the solvent, providing an increasingly more solvent-oil fraction. Following extraction, the solvent can be removed using methods known in the art. For example, distillation, rotary evaporation, or a rising film evaporator and steam stripper or any suitable desolventizer can be used for removing the solvent.

In one embodiment, the extracted lipids/fatty acids are exposed to an absorption process (e.g., bleaching) to remove one or more undesirable compounds such as, for example, color bodies and/or phosphatides that may be present. In some embodiments, the absorption process is a bleaching process comprising contacting the lipid/fatty acid extract with a bleaching material (e.g., neutral earth (e.g., natural clay or fuller's earth), acid-activated earth, activated carbon, activated clays, silicates, and or a combination thereof). The invention is not limited by the amount of bleaching material utilized.

In one embodiment, the extracted lipids/fatty acids are exposed to a degumming step. Degumming methods are known in the art and include, for example, water degumming, acid degumming, enzymatic degumming, and membrane degumming. In some embodiments, the lipid/fatty acid extract is subjected to degumming (e.g., following an absorption process), wherein the degumming comprises contacting the lipid/fatty acid extract with a mixture of aqueous acids that are in amounts effective to precipitate gums and/or chlorophyll-type compounds that may be present in the lipid/fatty acid extract composition. The invention is not limited by the type or amount of aqueous acids utilized. In one embodiment, the mixture of aqueous acids comprises sulfuric acid and/or phosphoric acid. In another embodiment, equal amounts of aqueous acids are mixed with the lipid composition. In a preferred embodiment, when blended with the oil, the aqueous acids are in an amount sufficient to provide an acidic pH. Precipitates that form after acid mixing can be removed from the lipid composition, for example using centrifugation and/or filtration (e.g., membrane filtration). In some embodiments, the degummed lipid/fatty acid extract composition is subjected to drying (e.g., to reduce moisture content of the composition). The invention is not limited by the drying condition (e.g., time, temperature, and/or a vacuum condition). As described herein, in some embodiments, the moisture content of the dried lipid/fatty acid composition is less than about 10% w/w (e.g., less than about 9, 8, 7, 6, 5, 4, 3, 2, 1, 0.9, 0.8, 0.7, 0.6, 0.5, 0.4, 0.3, 0.2, 0.1, 0.05, or 0.01% w/w).

Lipid Composition

In some embodiments, the invention provides a lipid composition prepared from a algal biomass of the invention. In some embodiments, the lipid composition is prepared in accordance with a method of the invention. For example, in some embodiments, a lipid composition is an algal biomass or a portion/fraction thereof from algae of the genus *Thraustochytrium*. In some embodiments, the algal biomass comprises an algae selected from *Dinophyceae, Cryptophyceae, Trebouxiophyceae, Pinguiophyceae*, and/or combinations thereof. In other embodiments, the algal biomass comprises an algae selected from *Thraustochytrium striatum, Thraustochytrium roseum, Thraustochytrium aureum, Crypthecodinium cohnii, Parietochloris* spp., *Rhodomonas* spp., *Cryptomonas* spp., *Parietochloris* spp., *Hemisebnis* spp.; *Porphyridium* spp., *Glossomastix* spp., and/or combinations thereof. In further embodiments, the algal biomass comprises an algae selected from *Parietochloris incise, Rhodomonas salina, Hemiselmis brunescens, Porphyridium cruentum* and *Glossomastix chrysoplasta*, and combinations thereof. In a preferred embodiment, the algal biomass comprises *Schizochytrium limacinum*.

Food Products and Animal Feed Additives

In some embodiments, a whole-cell algal biomass, fraction, and/or extract thereof is used for consumption (e.g., by a mammal (e.g., human or animal consumption)) or as a food additive (e.g., to increase the lipid content and/or nutritional components of a food). For example, in some embodiments, when used as animal feed (e.g., cattle feed, dairy feed, aquaculture feed, poultry feed, etc.), the lipids/fatty acids produced by an algal biomass of the invention is incorporated into a food product (e.g., animal feed). In some embodiments, a whole-cell algal biomass, fraction, and/or extract thereof is used for pharmaceutical or nutritional purposes and/or industrial applications.

The whole-cell algal biomass, fraction, and/or extract thereof can be provided in any one of variety of forms/compositions suitable for a particular application or use. In some embodiments, the whole-cell algal biomass, fraction, and/or extract thereof is provided. In another embodiment, a whole-cell algal biomass, fraction, and/or extract thereof is provided in a powdered form or as a free oil in a liquid form (e.g., lipid composition or a fraction or concentrate thereof). A whole-cell algal biomass, fraction, and/or extract thereof may be used for human and/or animal consumption. For example, in some embodiments, a whole-cell algal biomass, fraction, and/or extract thereof is provided as or incorporated into a feed, a dietary supplement, a food, a pharmaceutical formulation, a dairy product, and/or an infant formula.

For example, in one embodiment, a whole-cell algal biomass, fraction, and/or extract thereof is dried (e.g., spray drying, tunnel drying, vacuum drying) and used as a feed or food supplement for any animal or aquaculture organism (e.g., fish, shrimp, crab, lobster, etc.) whose meat and/or products are consumed by humans or animals (e.g., pets, livestock). In another embodiment, a whole-cell algal biomass, fraction, and/or extract thereof is mixed with a dry moisture-reducing agent (e.g., ground grain such as ground corn).

The compositions described herein may be used as a complete food product, as a component of a food product, as a dietary supplement or as part of a dietary supplement, as a feed additive and may be either in liquid, semisolid or solid form. The compositions of the invention additionally may be in the form of a pharmaceutical composition. The compositions, dietary supplements, food products, baby food products, feed additives, and/or pharmaceutical compositions of the invention may be utilized in methods for promoting the health of an individual. The compositions may be in liquid, semisolid or solid form. For example, the compositions may be administered as tablets, gel packs, capsules, gelatin capsules, flavored drinks, as a powder that can be reconstituted into such a drink, cooking oil, salad oil or dressing, sauce, syrup, mayonnaise, margarine or the like. Furthermore, the food product, dietary supplements, and the like, of the present invention can include, but are not limited to, dairy products, baby food, baby formula, beverages, bars, a powder, a food topping, a drink, a cereal, an ice cream, a candy, a snack mix, a baked food product and a fried food product. Beverages of the invention include but are not limited to energy drinks, nutraceutical drinks, smoothies, sports drinks, orange juice and other fruit drinks. A bar of the present invention includes, but is not limited to, a meal replacement, a nutritional bar, a snack bar and an energy bar, an extruded bar, and the like. Dairy products of the invention include, but are not limited to, including but not limited to yogurt, yogurt drinks, cheese and milk. Compositions intended for oral administration may be prepared according to any known method for the manufacture of dietary supplements or pharmaceutical preparations, and such compositions may include at least one additive selected from the group consisting of taste improving substances, such as sweetening agents or flavoring agents, stabilizers, emulsifiers, coloring agents and preserving agents in order to provide a dietetically or pharmaceutically palatable preparation. Vitamins, minerals and trace element from any physiologically acceptable source may also be included in the composition of the invention.

In some embodiments, a pharmaceutical composition of the invention comprises the compositions of the invention in a therapeutically effective amount. The compositions of the invention can be formulated for administration in accordance with known pharmacy techniques. See, e.g., Remington, The Science And Practice of Pharmacy (9th Ed. 1995). In the manufacture of a pharmaceutical composition according to the invention, the lipid compositions (including the physiologically acceptable salts thereof) is typically admixed with, inter alia, an acceptable carrier. The carrier will be compatible with any other ingredients in the formulation and must not be deleterious to the subject.

Biofuel

Many of the existing technologies for making biofuel from algae are expensive, inefficient and unsustainable when operated at a scale that is required to displace any meaningful fraction of petrodiesel in the market. The supply and expenditure of energy to harvest and process algae are often underestimated. To produce biodiesel from algae conventionally, the algae are typically harvested from a culture at a concentration of about 0.2 g/L in water. The harvested algae are then dewatered which increases the algal concentration to form an algal paste of about 15% solids. The paste is then fully dried by evaporating the water. Oil is then extracted from the dried algae with an organic solvent, such as hexane, which is removed by distillation from the algal oil. This conventional method for generating biodiesel from algae is prohibitively expensive.

For example, when algae grows in a natural body of water, the algal biomass is relatively dilute considering the volume of water. Producing a gallon of oil requires processing of about 20,000 to 40,000 gallons of water. The energy cost of transporting and processing such a large volume of water is high. As example, 2,500 gallons of oil/acre/year could be produced if algae with 25% of its mass as lipids could be produced at 25 g/m.sup.2/day. For this example, 50 million gallons of water must be processed to produce the 2,500 gallons of oil. The standard approach of pumping water to a centralized facility for dewatering is simply too energy-intensive and cost prohibitive. As example, a relatively small algal oil facility that produced 20 million gal/year would expend more energy pumping water from the pond to a central facility than that contained in the oil product, resulting in a net negative energy balance.

Accordingly, in some embodiments, the invention provides a method for preparing an algal biomass and/or lipid/fatty acid extract (e.g., a lipid/fatty acid composition) from an algal biomass, grown under conditions to contain elevated levels of total fat, the method comprising obtaining lipids from an algal biomass cultured under a culture condition sufficient to provide an algal biomass with elevated total fat content (e.g., total fat content greater than 67% of the biomass), wherein the algal biomass is harvested at a negative growth acceleration phase or a stationary phase of the algae. In another embodiment the algal biomass is harvested during a logarithmic growth phase of the algae. Methods for obtaining a lipid composition from an algal biomass of the invention are described herein.

Accordingly, in some embodiments, the invention provides a biofuel feedstock or a biofuel comprising lipids, hydrocarbons, or both, derived from an algal culture and/or algal biomass generated according to the methods of the invention. In some embodiments, lipids or algal compositions comprising the same are subdivided according to polarity: neutral lipids and polar lipids. The major neutral lipids are triglycerides and free saturated and unsaturated fatty acids. The major polar lipids are acyl lipids, such as glycolipids and phospholipids. Is some embodiments, a composition comprising lipids and hydrocarbons of the invention is described and distinguished by the types and relative amounts of fatty acids and/or hydrocarbons present in the composition. In some embodiments, the hydrocarbons present in algae compositions of the invention are mostly straight chain alkanes and alkenes, and may include paraffins and the like having up to 36 carbon atoms.

In some embodiments, the invention provides a method of making a liquid fuel that comprise processing lipids derived from an algal culture and/or algal biomass or lipid fraction thereof described herein. Products of the invention made by the processing algal derived biofuel feedstocks can be incorporated or used in a variety of liquid fuels including but not limited to, diesel, biodiesel, kerosene, jet-fuel, gasoline, JP-1, JP-4, JP-5, JP-6, JP-7, JP-8, Jet Propellant Thermally Stable (JPTS), Fischer-Tropsch liquids, alcohol-based fuels including ethanol-containing transportation fuels, other biomass-based liquid fuels including cellulosic biomass-based transportation fuels.

In some embodiments, triacylglycerides in algal oil is converted to fatty acid methyl esters (FAME or biodiesel), for example, by using a base-catalyzed transesterification process (for an overview see, e.g., K. Shaine Tyson, Joseph Bozell, Robert Wallace, Eugene Petersen, and Luc Moens, "Biomass Oil Analysis: Research Needs and Recommendations, NREL/TP-510-34796, June 2004, hereby incorporated by reference in its entirety). In some embodiments, the triacylglycerides are reacted with methanol in the presence of NaOH at 60 C. for 2 hrs to generate a fatty acid methyl ester (biodiesel) and glycerol. In further embodiments, the biodiesel and glycerol co-products are immiscible and typically separated downstream through decanting or centrifugation, followed by washing and purification. Free fatty acids (FFAs) are a natural hydrolysis product of triglyceride and formed by reacting triacylglycerides and water. In some embodiments, methods of the invention further comprise a step for quickly and substantially drying the algal oil by techniques known in the art to limit production of free fatty acids, preferably to less than 1%. In another embodiment of the invention, the methods can further comprise a step for converting or removing the free fatty acids by techniques known in the art.

In some embodiments, triacylglycerides in algal oil is converted to fatty acid methyl esters (FAME or biodiesel) by acid-catalyzed transesterification, enzyme-catalyzed transesterification, or supercritical methanol transesterification. Supercritical methanol transesterification does not require a catalyst (See, e.g., Kusdiana, D. and Saka, S., "Effects of water on biodiesel fuel production by supercritical methanol treatment," Bioresource Technology 91 (2004), 289-295; Kusdiana, D. and Saka, S., "Kinetics of transesterification in rapeseed oil to biodiesel fuel as treated in supercritical methanol," Fuel 80 (2001), 693-698; Saka, S., and Kusdiana, D., "Biodiesel fuel from rapeseed oil as prepared in supercritical methanol," Fuel 80 (2001), 225-231). The reaction in supercritical methanol reduces the reaction time from 2 hrs to 5 minutes. In addition, the absence of the base catalyst NaOH greatly simplifies the downstream purification, reduces raw material cost, and eliminates the problem with soaps from free fatty acids. Rather than being a problem, the tree fatty acids become valuable feedstocks that are converted to biodiesel in the supercritical methanol as follows.

In some embodiments, triacylglycerides are reduced with hydrogen to produce paraffins, propane, carbon dioxide and water, a product generally known as green diesel. The paraffins can either be isomerized to produce diesel or blended directly with diesel. In some embodiments, there are advantages of hydrogenation over conventional base-catalyzed transesterification. For example, the hydrogenation process (also referred to as hydrocracking) is thermochemical and therefore much more robust to feed impurities as compared to biochemical processes (e.g., hydrocracking is relatively insensitive to free fatty acids and water). Free fatty acids are readily converted to paraffins, and water simply reduces the overall thermal efficiency of the process but does not significantly alter the chemistry. In another non-limiting example, the paraffin product is a pure hydrocarbon, and therefore indistinguishable from petroleum-based hydrocarbons. Unlike biodiesel which has a 15% lower energy content and can freeze in cold weather, green diesel has similar energy content and flow characteristics (e.g., viscosity) to petroleum-based diesel. In various embodiments, the methods of the invention encompass the steps of hydrocracking and isomerization, which are well known in the art to produce liquid fuels, such as jet-fuel, diesel, kerosene, gasoline, JP-1, JP-4, JP-5, JP-6, JP-7, JP-8, and JPTS.

EXPERIMENTAL

The following examples are provided in order to demonstrate and further illustrate certain preferred embodiments and aspects of the present invention and are not to be construed as limiting the scope thereof.

Example 1

Growth of High Fat Algal Biomass

Experiments were conducted during development of embodiments of the invention in order to characterize and establish methods for heterotrophic algae production, and in particular, methods of culturing algae in order to generate an algal biomass containing high fat/lipid levels. A series of conventional heterotrophic algae production studies was performed and run in batch.

A culture of *Schizochytrium limacinum* was obtained and stored in 1.5 mL cryovials at −80 C. For each experiment, the process was started by thawing cryovials and aseptically adding to 1.0 L shake flasks of with media. Media in the 1 L flasks contained 50 g/L sugar, 10 g/L yeast extract, and 4 g/L sea salt. Three liters of 3 to 6 day old shake flask culture was used to inoculate a 250 L vessel containing media, grown for 24-48 hours, and then transferred to a main vessel (17,000 to 28,000 L) and run as a batch process for 36 to 72 hours. The temperature of the batch runs was kept between 25 and 30 C. The temperature range was large due to lack of precise control of the system. The media used in the seed (250 L) and batch (17,000 to 28,000 L) runs was as follows:

TABLE 1A

Media used in traditional batch and seed cultures.

| Raw material | Batched |
|---|---|
| Sugar | 50 g/L |
| Yeast Extract | 7.5 g/L |
| MgSO4 | 0.1538 g/L |
| Urea | 2 g/L |
| CaCl2 | 0.1538 g/L |
| MgCl2 | 0.1538 g/L |
| Antifoam | 0.3 ml |

Total fat content of the algal biomass of the batch cultures was determined by gas chromatography (See AOAC gravimetric method 922.06), acid hydrolysis (See Total Fat by Acid Hydrolysis Ankom Technology Method 1, Feb. 10, 2009), and High Temperature Solvent Extraction (See Ankom Technology Method 2, Jan. 30, 2009 and AOCS Method 5-04). In brief, a typical analysis procedure for fermentation broth was as follows: Broth samples were concentrated by centrifugation. After decanting, the sample was freeze dried for 24 hours with resultant moisture less than one percent. The samples were weighed prior to acid hydrolysis, washed and dried in an oven. This was followed by an extraction process under gradient thermal conditions with petroleum ether. The hydrolysis and extraction process were undertaken utilizing automated instruments. After further drying, results were determined on the basis of mass loss.

As shown in Table 1B below, the total fat/lipid levels (w/w) achieved in the batch productions at a temperature range from 25-30 C was 8-38%.

TABLE 1B

Total fat content of algal biomass grown in batch run between 25-30 C.

| Log run # | Total fat (%) |
|---|---|
| A-1-10 | 33.75 |
| A-2-10 | 38.59 |
| A-3-10 | 27.30 |
| A-4-10 | 38.51 |
| A-5-10 | 7.82 |
| A-7-10 | 33.33 |
| A-8-10 | 34.85 |
| A-9-10 | 27.21 |

Efforts were made to increase the amounts of fat/lipid levels as these amounts were considered too low to be of value and additional experiments were ran in an effort to increase the level of lipids produced in cultured algae.

During development of embodiments of the invention, experiments were conducted in order to determine if changes in the constituents and/or amounts or ratios of the same in the media could provide different algal growth characteristics. In addition, experiments were conducted to determine if scale-up of an algal culture system would alter algal growth characteristics. In particular, the amounts and ratios of $MgSO_4$, Urea, $CaCl_2$, $MgCl_2$, and $KH_2PO_4$ were modified in an attempt to increase the level of lipid produced by cultured algae.

Results of fermentations produced in a batch volume of 10 L are shown below:

TABLE 2

10 L fermentation conditions and results.

| lab trial runs - 10 L Ingredients/log # | NB4-030311 | NB6-030311 | NB4-032311 | NB6-032311 | NB3-032811 | NB4-032811 |
|---|---|---|---|---|---|---|
| (g/L) | | | | | | |
| Sugar | 50 | 50 | 50 | 50 | 50 | 50 |
| Yeast Extract | 7.5 | 7.5 | 7.5 | 7.5 | 7.5 | 7.5 |
| MgSO4 | 0.1538 | 0.1538 | 0.1538 | 0.1538 | 0.5 | 1 |
| NaCl | 0 | 0 | 0 | 0 | 0 | 0 |
| Urea | 2 | 2 | 2 | 2 | 1 | 1 |
| ZnSO4 | 0.1538 | 0.1538 | 0.1538 | 0.1538 | 0.1538 | 0.1538 |
| CaCl2 | 0.1538 | 0.1538 | 0.1538 | 0.1538 | 1 | 2 |
| MgCl2 | 0.1538 | 0.1538 | 0.1538 | 0.1538 | 0.5 | 1 |
| KH2PO4 | — | — | 1.5 | 1.5 | 0.5 | 1 |
| Trace (liquid) - ml Ferric Chloride Zn sulfate Mn sulfate Boric acid Copper sulfate | 10 | 10 | 10 | 10 | 20 | 20 |
| Feed | | | | | | |
| Urea:KH2PO4 | urea 200 g/L | urea 200 g/L | 2:1 | 2:1.5 | 2:0.5 | 2:0.5 |
| temp set point | 30 | 30 | 30 | 30 | 30 | 30 |
| fat % | 8.13 | 6.89 | 88.98 | 84.28 | 56.1 | 64.3 |
| Notes | strong NH3 smell ph issues foam out | strong NH3 smell ph issues foam out | | | | |

TABLE 3

Additional 10 L fermentation conditions and results.

| Ingredients/log # | NB6-032811 | NB3-040711 | NB4-040711 | NB6-040711 | NB3-041911 | NB4041911 | NB6041911 |
|---|---|---|---|---|---|---|---|
| (g/L) | | | | | | | |
| Sugar | 50 | 50 | 50 | 50 | 50 | 50 | 50 |
| Yeast Extract | 7.5 | 7.5 | 7.5 | 5 | 7.5 | 7.5 | 6.25 |
| MgSO4 | 2 | 2 | 2 | 2 | 2 | 2 | 2 |
| NaCl | 0 | 0 | 0 | 0 | 0 | 0 | 0 |
| Urea | 1 | 1 | 1 | 1 | 1 | 1 | 1 |
| ZnSO4 | 0.1538 | 0.1538 | 0.1538 | 0.1538 | 0 | 0 | 0 |
| CaCl2 | 4 | 4 | 4 | 4 | 4 | 4 | 4 |
| MgCl2 | 2 | 2 | 2 | 2 | 2 | 2 | 2 |
| KH2PO4 | 2 | 0.25 | 0.25 | 0.25 | 0.25 | 0.25 | 0.25 |
| Trace (liquid) - ml Ferric Chloride Zn sulfate | 20 | 20 | 20 | 20 | 20 | 20 | 20 |

TABLE 3-continued

Additional 10 L fermentation conditions and results.

| Ingredients/log # | NB6-032811 | NB3-040711 | NB4-040711 | NB6-040711 | NB3- 041911 | NB4041911 | NB6041911 |
|---|---|---|---|---|---|---|---|
| Mn sulfate | | | | | | | |
| Boric acid | | | | | | | |
| Copper sulfate | | | | | | | |
| Feed | | | | | | | |
| Urea:KH2PO4 | 2:0.5 | 2:0.5 | 2:0.5 | 2:0.5 | | | |
| temp set point | 30 | 30 | 30 | 30 | 30 | 30 | 30 |
| fat % | 73.7 | 71.16 | 73.49 | 73.88 | 68.69 | 76.56 | 72.56 |

TABLE 4

Additional 10 L fermentation conditions and results.

| Ingredients/log # | NB3061411 | NB4061411 | NB6061411 | NB3062111 | NB4062111 | NB6032111 | NB3062811 | NB4062811 | NB6032811 |
|---|---|---|---|---|---|---|---|---|---|
| (g/L) | | | | | | | | | |
| Sugar | 50 | 50 | 50 | 50 | 50 | 50 | 50 | 50 | 50 |
| Yeast Extract | 7.5 | 7.5 | 7.5 | 7.5 | 7.5 | 7.5 | 7.5 | 7.5 | 7.5 |
| MgSO4 | 0.1538 | 2 | 2 | 2 | 2 | 2 | 0.1538 | 2 | 2 |
| NaCl | 0 | 0 | 0 | 4 | 8 | 0 | 0 | 0 | 0 |
| Urea | 2 | 1 | 1 | 1 | 1 | 1 | 1 | 1 | 1 |
| ZnSO4 | 0.1538 | 0.1538 | 0 | 0 | 0 | 0 | 0 | 0 | 0 |
| CaCl2 | 0.1538 | 4 | 4 | 4 | 4 | 4 | 4 | 0.1538 | 4 |
| MgCl2 | 0.1538 | 2 | 2 | 2 | 2 | 2 | 2 | 2 | 0.1538 |
| KH2PO4 | 2 | 0.25 | 0.25 | 0.25 | 0.25 | 0.25 | 0.25 | 0.25 | 0.25 |
| Trace (liquid) - ml | 10 | 10 | 0 | 0 | 0 | 0 | 0 | 0 | 0 |
| Ferric Chloride | | | | | | | | | |
| Zn sulfate | | | | | | | | | |
| Mn sulfate | | | | | | | | | |
| Boric acid | | | | | | | | | |
| Copper sulfate | | | | | | | | | |
| Feed | | | | | | | | | |
| Urea:KH2PO4 | 2:0.5 | 2:0.5 | 2:0.5 | 2:0.5 | 2:0.5 | 2:0.5 | 2:0.5 | 2:0.5 | 2:0.5 |
| temp set point | 30 | 30 | | | | | | | |
| fat % | 46.52 | 65.04 | 67.61 | 61.28 | 62.95 | 68.53 | 49.25 | 54.41 | 64.97 |
| | Fomular confirmation | | | NaCl effects | | | Salt ratio effects | | |

These experiments, conducted during development of embodiments of the invention, indicated that certain amounts/ratios of substrates present within the media had a direct impact on algal growth characteristics (e.g., total biomass achieved as well as amount of fat and/or other component content within the biomass itself). Parameters that provided a high fat content biomass in the 10 L runs were then utilized to determine if they would be successful for large scale production of a high fat content biomass.

Example 2

Large Scale Production of High Fat Algal Biomass

The initial attempts to generate a heterotrophic algal biomass described in Example 1 above utilized procedures based on yeast fermentation processes. The processes were run in batch due to limitations in the production facility (Nicholasville, Ky.) and temperatures that could only be controlled between 25 and 30 C. The temperature range was large due to lack of precise control of the system. As indicated in Table 1, above, the fat levels achieved at the Nicholasville, Ky. plant ranged from 8-38%. However, as indicated above, additional experiments were carried out during development of embodiments of the invention that provided the identification of certain ratios/amounts of substrates that could be utilized during heterotrophic algal biomass production to alter algal growth and biomass generation/properties. Modification of the levels and ratios of the media (e.g., $MgSO_4$, Urea, $CaCl_2$, $MgCl_2$, and $KH_2PO_4$) during fermentation was identified and characterized to alter algal growth, and to generate a biomass with significantly different properties (e.g., a significantly higher fat content biomass). As described below, the process (including media containing the identified ratios/amounts of substrates effective in generating a high fat content algal biomass (e.g., greater than 67% fat content)) was further tested and run in large scale and also as a fed-batch (thereby allowing for modification and control of amounts of nitrogen, phosphorus, potassium, and carbon during the ran).

A culture of Schizochytrium limacinum was obtained and stored in 1.5 mL cryovials at −80 C. For each culture, a cryovial was thawed and aseptically added to 1.0 L shake flask of media. Media in the 1 L flasks contained the components as shown in Table 5:

TABLE 5

Media used for 1.0 L culture.

| Ingredient | Batched | Manufacturer |
| --- | --- | --- |
| Sugar | 50 g/L | Cargill - Hammond, IN, USA |
| Yeast Extract | 10 g/L | Sensient - Indianapolis, IN, USA |
| Sea Salt | 4 g/L | Sigma-Aldrich - St. Louis, MO USA |

The temperature of the shake flasks containing *Schizochytrium limacinum* in media was kept at 30 C and shaken at 250 RPM until such time that the algae had entered logarithmic/exponential growth phase but prior to depletion of glucose in the media (usually 72-144 hours).

The contents of 1 L culture flasks were then aseptically transferred into 2.0 L aspirator bottles with sterile connectors that were used to connect to larger vessels (40 L or 27 L or 18 L vessels). Thus, the 1 L culture flask cultures were used as inoculum and aseptically added to a seed vessel (either 40 L or 27 L or 18 L) containing media described in Table 6 below:

TABLE 6

Media used for 18 L or 27 L, first seed cultures.

| Ingredient | g/L | Manufacturer |
| --- | --- | --- |
| Sugar | 50 | Cargill - Hammond, IN, USA |
| Yeast Extract | 7.5 | Sensient - Indianapolis, IN, USA |
| MgSO4 | 0.1538 | Norkem Limited - Kutahya, Turkey |
| CaCl2 | 0.1538 | Occidental Chemical Company - Dallas, TX |
| MgCl2 | 0.1538 | North American Salt Company - Overland Park, KS |

The first seed stage (40/18/27 L) was run at 30 C, under airflow and agitation conditions so as to maintain dissolved oxygen at or above 10%, and until at least 20 g/L of glucose was consumed. When grown under sterile conditions, no pH control was required. Rather, the pH stayed within a healthy range throughout the fermentation process. The first seed stage (40/18/27 L) was considered completed when algal growth was within log/exponential growth stage, glucose had not been depleted from the media, but at least 20 g/L of glucose had been consumed (in general, this occurred between about 24-48 hours). A larger vessel (4000/2000 L) was made ready for the first seed stage culture (e.g., it was filled with media and brought to 30 C under sterile conditions).

Upon completion of the first seed culture, the contents of the first seed stage (40/18/27 L) culture vessel was transferred to a vessel with at least 2,000 L media described in Table 7 below

TABLE 7

Media used for 4,000/2000 L, second seed cultures.

| Ingredient | g/L | Manufacturer |
| --- | --- | --- |
| Sugar | 50 | Cargill - Hammond, IN, USA |
| Yeast Extract | 7.5 | Sensient - Indianapolis, IN, USA |
| MgSO4 | 0.1538 | Norkem Limited - Kutahya, Turkey |
| CaCl2 | 0.1538 | Occidental Chemical Company - Dallas, TX |
| MgCl2 | 0.1538 | North American Salt Company - Overland Park, KS |

This second seed stage (4000/2000 L) culture was run at 30 C, under airflow and agitation conditions so as to maintain dissolved oxygen at or above 10%, and until at least 20 g/L of glucose was consumed. When grown under sterile conditions, no pH control was required. Rather, the pH stayed within a healthy range throughout the fermentation process. The second seed stage (4000/2000 L) was considered completed when algal growth was within log/exponential growth stage, glucose had not been depleted from the media, but at least 2.0 g/L of glucose had been consumed (in general, this occurred between about 24-48 hours).

Upon completion of the second seed (4000/2000 L) culture, the contents of the second seed culture were aseptically transferred into a third culture vessel with a volume ranging between 70,000 L to 220,000 L of sterile media at 30 C as described in Table 8 below:

| Batch | | |
| --- | --- | --- |
| Raw material | Batched | Manufacturer |
| Sugar | 50 g/L | Cargill - Hammond, IN, USA |
| Yeast Extract | 7.5 g/L | Sensient - Indianapolis, IN, USA |
| MgSO4 | 4 g/L | Norkem Limited - Kutahya, Turkey |
| Urea | 1 g/L | PCS Sales - Northbrook, IL |
| CaCl2 | 2 g/L | Occidental Chemical Company - Dallas, TX |
| MgCl2 | 2 g/L | North American Salt Company - Overland Park, KS |
| $KH_2PO_4$ | 0.25 g/L | Lidochem - Hazlet, NJ |

When 30 g/L of glucose had been consumed by algae present in the third culture vessel (70,000-220,000 L vessel), glucose and fed-batch feeds were started. Glucose was maintained at 10 g/L during large scale culture of algae in the third culture vessel (70,000-220,000 L vessel). As described in Table 9 below, the feed used for the fed-batch process contained:

TABLE 9

Feed used for fed-bath process.
Feed

| Ingredient | g/L | Manufacturer |
| --- | --- | --- |
| Urea | 2 g/L | PCS Sales - Northbrook, IL |
| $KH_2PO_4$ | 0.5 g/L | Lidochem - Hazlet, NJ |

The fed batch feed was added over a 34 hour period. Although an understanding of the mechanism is not needed to practice the present invention, and while the present invention is not limited to any particular mechanism of action, in some embodiments, this time period was identified based upon the observation that it took 20 hours for the feed to start (for 30 g/L of glucose to be consumed by the algae present in the third culture vessel). The feed was then stopped (e.g., at around log hour 54) in order to allow all of the nutrients to be removed (consumed) from the media. Harvest of the algal biomass took place upon the termination of exponential growth, occurring generally between the log hours 66-76.

The culture broth was de-sludge centrifuged under conditions to achieve 15-30% solids, with the concentrate spray dried to remove water to a final moisture of less than 5%.

Results of several independent, large scale cultures are shown in FIG. 1 and Tables 10-12 below:

TABLE 10

Large scale production culture results.

| Run number | Fat % (harvest sample) | Vol adjusted Biomass (g/L) | % recovery from centrifuge | Fat % (spray dried product) | Protein % (spray dried Product) | Moisture % spray dried product |
|---|---|---|---|---|---|---|
| F1-2-11 | 60.7* | 86.2 | | 75.7 | 11.66 | 1.47 |
| F1-3-11 | 69.64 | 86.4 | 55 | 70.25 | 16.47 | 1.37 |
| F1-4-11 | 74.76 | 66.5 | 67 | 71.56 | 15.92 | 2.11 |
| F1-5-11 | 73.12 | 70.8 | 68 | 65.65 | 17.14 | 2.43 |
| F1-6-11 | 62.77** | 45.7 | 89 | 54.8 | 13.35 | 2.14 |

TABLE 10-continued

Large scale production culture results.

| Run number | Fat % (harvest sample) | Vol adjusted Biomass (g/L) | % recovery from centrifuge | Fat % (spray dried product) | Protein % (spray dried Product) | Moisture % spray dried product |
|---|---|---|---|---|---|---|
| F2-1-11 | 72.59 | 50.9 | 87 | 65.89 | 17.64 | 2.72 |
| F2-2-11 | 70.81 | 59.5 | 52 | 66.49 | 15.29 | 2.15 |

*bad harvest sample
**process control problems with this batch
F1-2-11 Had a batch volume of 70,000 L and a harvest volume of 93,700 L
F1-3-11 Had a batch volume of 70,000 L and a harvest volume of 84,000 L
F1-4-11 Had a batch volume of 70,000 L and a harvest volume of 92,300 L
F1-5-11 Had a batch volume of 70,000 L and a harvest volume of 82,300 L
F1-6-11 Had a batch volume of 80,000 L and a harvest volume of 83,600 L
F2-1-11 Had a batch volume of 110,000 L and a harvest volume of 113,000 L
F2-2-11 Had a batch volume of 110,000 L and a harvest volume of 125,600 L The biomass generated from each large scale, fed-batch culture was characterized, including analysis of the total fat (saturated and unsaturated fat) content; moisture, docosahexaenoic acid (DHA)content, palmitic acid content, crude protein content and ash content (See, e.g., Fat content and/Moisture—AOCS Am 5-04 'Rapid Determination of Oil/Fat Utilizing High Temperature Solvent Extraction' v. 3/31/10; DHA/Palmitic—AOCS Method Ce 1 b-89 and AOAC Method of Analysis 991.39; Protein—AOAC 990.03; Ash—AOAC 942.05 Vol adjusted Biomass (g/L)—Stone, et. al. Dry Weight Measurement of Microbial Biomass and Measurement Variablity Analysis. Biotechnology Techniques. Vol 6: 207-212.

TABLE 11

Table 11. Characterization of large scale cultures

| Run #/Comments | TOTAL FAT % (Final Harvest) | Moisture (%) Max 6% | DHA (mg/g) | Palmitic (mg/g) | Crude Protein (%) Report on release | Ash max 10% |
|---|---|---|---|---|---|---|
| SL-F1-1-11 | 72.70 | 1.39 | 191.8 | 379 | 14.96 | 3.5 |
| SL-F1-3-11 | 69.64 | 1.37 | 181.1 | 366.2 | 16.47 | 3.08 |
| SL-F1-4-11 | 73.71 | 2.11 | 185.8 | 373.8 | 15.92 | 3.11 |
| SL-F1-5-11 | 73.12 | 2.43 | 176.8 | 351.3 | 17.14 | 0.0373 |
| SL-F2-1-11 | 72.59 | 2.72 | 252.4 | 360.9 | 17.64 | 0.0363 |
| SL-F2-2-11 | 70.81 | 2.15 | 247.2 | 365 | 15.29 | 0.041 |
| SL-F2-3-11 | 72.86 | 2.50 | 197.36 | 269.4 | 11.58 | 3.29 |
| SL-F2-4-11 | 69.03 | 3.07 | 177.9 | 133.65 | 18.23 | 3.9 |
| SL-F2-5-11 | 70.10 | 2.12% | 203.24 | 193.99 | 10.93 | 0.0342 |
| SL-F2-6-11 | 73.55 | 2.61 | 203.99 | 206.67 | 12.01 | 3.34 |
| SL-F2-8-11 | 70.86 | 1.91 | 190.31 | 287.79 | 12.71 | 3.3 |
| SL-F2-9-11 | 76.89 | 1.68 | 191.69 | 227.52 | 9.62 | 3 |
| SL-F1-8-11 | 76.31 | 1.55 | 191.41 | 318 | 10.71 | 3.8 |
| SL-F2-10-11 | 72.15 | 1.75 | 186.24 | 256.13 | 13.37 | 4.81 |
| SL-F2-11-11 | 73.64 | 2.49 | 184.34 | 299.77 | 11.45 | 4.42 |
| SL-F1-9-11 | 75.57 | 1.28 | 202.51 | 250.01 | 10.02 | 3.48 |
| SL-F2-13-11 | 70.95 | 1.66 | 182.82 | 326.94 | 12.39 | 4.59 |
| SL-F2-14-11 | 69.13 | 1.42 | 196 | 253.11 | 14.79 | 3.65 |
| SL-F1-13-11 | 67.56 | 1.73 | 184.66 | 212.92 | 15.1 | 3.97 |
| SL-F1-14-11 | 68.57 | 1.23 | 170.16 | 89.35 | 11.86 | 4.22 |
| SL-F3-4-11 | 68.8 | 1.56 | 203.25 | 183.65 | 15.31 | 3.84 |
| SL-F1-15-11 | 70.58% | 1.14 | 175.58 | 147.37 | 9.8 | 3.56 |
| SL-F1-16-11 | 72.72 | 1.31 | 175.28 | 91.4 | 10.43 | 4.06 |
| SL-F3-8-11 | 71.75 | 1.8 | 207.95 | 138.37 | 14.32 | 3.65 |
| SL-F5-5-11 | 68.7 | 1.23 | 189.07 | 119.72 | 11.68 | 3.42 |
| SL-F1-25-11 | 74.80 | 1.54 | | | 9.16 | 3.68 |
| SL-F3-14-11 | 76.24 | 1.90 | | | 8.41 | 3.08 |
| SL-F3-15-11 | 75.80 | 1.08 | | | 7.3 | 3.26 |
| SL-F1-1-12 | 70.24 | | | | 8.3 | 3.51 |

TABLE 12

Table 12. Characterization of large scale cultures

| Run #/Comments | TOTAL FAT % (Final Harvest) | Moisture (%) Max 6% | DHA (mg/g) | Palmitic (mg/g) | Crude Protein (%) Report on release | Ash max 10% |
|---|---|---|---|---|---|---|
| SL-F1-25-11 | 74.80 | 1.54 | 170.63 | 355.6 | 9.16 | 3.68 |
| SL-F3-14-11 | 76.24 | 1.90 | 179.85 | 346.41 | 8.41 | 3.08 |
| SL-F3-15-11 | 75.80 | 1.08 | 182.81 | 367.01 | 7.3 | 3.26 |
| SL-F1-1-12 | 70.24 | 1.81 | 160.84 | 336.77 | 8.3 | Released |
| SL-F4-1-12 | 68.53 | 1.71 | 189.06 | 332.29 | 10.26 | 3.56 |
| SL-F6-2-12 | 69.13 | 1.73 | 169.44 | 351.39 | 7.75 | 3.11 |
| SL-F5-2-12 | 75.00 | 1.84 | 175.05 | 371.57 | 6.89 | 3.5 |
| SL-F4-2-12 | 69.10 | 1.84 | 198.24 | 341.94 | 8.85 | 3.88 |
| SL-F6-3-12 | 69.34 | 1.80 | 175.42 | 340.86 | 10.44 | 3.62 |
| SL-F5-3-12 | 67.28 | 3.61 | 176.61 | 360.01 | 10.19 | 3.56 |
| SL-F1-2-12 | 71.09 | 1.72 | 154.22 | 371.31 | 12.56 | 3.78 |
| SL-F1-4-12 | 68.42 | 1.66 | 159.54 | 375.93 | 12.88 | 3.81 |
| SL-F4-5-12 | 70.89 | 1.88 | 171.73 | 397.13 | 12.38 | 3.1 |
| SL-F6-6-12 | 70.38 | 1.8 | 155.05 | 377.11 | 12.56 | 3.71 |
| SL-F5-6-12 | 68.17 | 1.75 | 155.73 | 389.31 | 10.56 | 3.8 |
| SL-F3-3-12 | 73.64 | 1.94% | 156.25 | 393.08 | 12.13 | 3.52 |
| SL-F1-7-12 | 71.97 | 1.58 | 164.05 | 362.4 | 8.75 | 3.98 |
| SL-F3-4-12 | 70.93 | 2.37 | 183.88 | 366.83 | 10.13 | 2.23 |
| SL-F6-7-12 | 70.95 | 2.66 | 176.68 | 366.29 | 10.56 | 4.31 |
| SL-F1-8-12 | 72.08 | 1.94 | 172.91 | 407.2 | 9 | 3.62 |
| SL-F3-6-12 | 72.15 | 1.85 | | | 10.56 | 7.56 |
| SL-F3-7-12 | 69.63 | 2.42 | | | 10.57 | 3.67 |
| SL-F3-8-12 | 71.77 | 1.78 | | | | |
| SL-F3-9-12 | 69.18 | 1.74 | | | | |

Additionally, the fatty acid profile of the biomass was characterized. As shown in FIG. 2, the fatty acid profile of each algal biomass generated is highly similar/consistent, independent of the total fat content of the biomass. A composite fatty acid profile, taking into consideration the collective profiles of all samples analyzed, is provided in FIG. 3.

The glyceride profile was also determined for each algal biomass. Of the total glyceride content of the biomass, about 4-8% were diglycerides, less than 1% glycerol, about 3-7% monoglycerides and about 84-88% triglycerides.

Example 3

Biomass Harvesting

Experiments conducted during development of embodiments of the invention identified that the increased total fat levels in the biomass caused significant problems with regard to centrifugation of the algal biomass. Recovery of biomass content post-centrifugation ranged from only about 45-85% total biomass weight. This is shown, for example, in Table 13 below:

TABLE 13

Comparison of Fat and Protein yield from direct harvest sample versus spray dried product.

| Run number | Fat % (harvest sample) | Vol adjusted Biomass (g/L) | Protein % (harvest sample) | % recovery from centrifuge | Fat % (spray dried product) | Protein % (spray dried Product) | Moisture % spray dried product |
|---|---|---|---|---|---|---|---|
| F1-2-11 | 60.7* | 86.2 | NA | NA | 75.7 | 11.66 | 1.47 |
| F1-3-11 | 69.64 | 86.4 | NA | 55 | 70.25 | 16.47 | 1.37 |
| F1-4-11 | 74.76 | 66.5 | NA | 67 | 71.56 | 15.92 | 2.11 |
| F1-5-11 | 73.12 | 70.8 | 16.14 | 68 | 65.65 | 17.14 | 2.43 |
| F1-6-11 | 62.77** | 45.7 | NA | 89 | 54.8 | 13.35 | 2.14 |
| F2-1-11 | 72.59 | 50.9 | 16.29 | 87 | 65.89 | 17.64 | 2.72 |
| F2-2-11 | 70.81 | 59.5 | 12.58 | 52 | 66.49 | 15.29 | 2.15 |

*bad harvest sample ** process control problems with this batch
F1-2-11 Had a batch volume of 70,000 L and a harvest volume of 93,700 L
F1-3-11 Had a batch volume of 70,000 L and a harvest volume of 84,000 L
F1-4-11 Had a batch volume of 70,000 L and a harvest volume of 92,300 L
F1-5-11 Had a batch volume of 70,000 L and a harvest volume of 82,300 L
F1-6-11 Had a batch volume of 80,000 L and a harvest volume of 83,600 L
F2-1-11 Had a batch volume of 110,000 L and a harvest volume of 113,000 L
F2-2-11 Had a batch volume of 110,000 L and a harvest volume of 125,600 L The recovery problems were identified to be attributable to the increase in the amount of low density lipid/oil in the biomass. Thus, experiments were conducted during embodiments of the invention in an effort to address this problem.

One approach that displayed the ability to enhance recovery of the biomass was to chill the culture comprising the algal biomass prior to centrifugation. Although an understanding of a mechanism is not needed to practice the invention, and the invention is not limited to any particular mechanism of action, in some embodiments, chilling the culture increased the density of the lipid/oil and allowed a larger recovery of the biomass.

Experiments were conducted in order to determine the effects of chilling the biomass before centrifugation.

Lab trial one: 2 gallons of broth collected and stored at 7-8 C for 16 plus hours. Eight X 50 ml centrifuge tubes were collected and placed in a water bath to reach target temperatures described in table 14 below. All samples were centrifuged at 5000 rpm for 5 minutes.

TABLE 14

Culture temperature and centrifugation results of trail 1.

| Temperature (C.) | Visual Observation |
| --- | --- |
| 10 | Excellent separation with no floating cells. Clear supernatant. |
| 20 | Good separation with no floating cells. Cloudier than 10 C. |
| 25 | Similar to 20 C.; cloudier |
| 30 | Good separation with no floating cells; cloudier |
| 35 | Good separation with no floating cells; very cloudy |
| 40 | Still separating; floating cells; milky supernatant |
| 45 | Poor separation |
| 50 | Almost no separation with numerous floating cells |

Lab trial 2: Fresh broth samples were collected and tested over a temperature range of 10-30 C. They were not refrigerated overnight as in trial 1. All samples were allowed to sit in an ice water bath to target temperature. Samples were centrifuged at 5000 rpm for 5 minutes.

TABLE 13

Culture temperature and centrifugation results of trail 2.

| Temperature (C.) | Visual Observation | Density (g/ml) |
| --- | --- | --- |
| 10 | Excellent separation with no floating cells. Clear supernatant. | 1.01967 |
| 15 | Good separation with no floating cells. Very cloudy supernatant | |
| 20 | Sample still separating; visible flocculation. | |
| 25 | Very similar to 20 C.; increasing cloudiness | |
| 30 | Still Good separation; increasing cloudiness | 1.02915 |

As described in Example 2 and FIG. 1, during large scale production, chilling of the biomass prior to recovery (centrifugation) lead to significant increase in total recovery of the biomass. Multiple large scale runs have been completed with total recovery of approximately 95%.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

What is claimed is:

1. A process of making an algal biomass comprising at least 67% total fat comprising culturing an algae in two or more types of culture medium sequentially, and wherein said culturing comprises:
culturing the algae in a culture medium comprising a carbon source, yeast extract, a magnesium source, and a calcium source; and subsequently, culturing the algae in a culture medium comprising a carbon source, a yeast extract, a nitrogen source, a phosphate source, a magnesium source, a calcium source, and 4 g/L or less of sodium chloride, wherein the nitrogen and phosphate are in a ratio of 50:1 to 4:1, and wherein the type of algae is selected from the group consisting of Thraustochytrium, Schizochytrium, and Aurantiochytrium.

2. The process of claim 1, wherein one culture medium of the two or more types of culture medium contains 50 g/L of a carbon source, 7.5 g/L yeast extract, 0.15 g/L magnesium sulfate, 0.15 g/L calcium chloride and 0.15 g/L magnesium chloride.

3. The process of claim 2, wherein the carbon source is a sugar.

4. The process of claim 3, wherein the sugar is glucose.

5. The process of claim 1, wherein one culture medium of the two or more culture medium contains 50 g/L of a carbon source, 7.5 g/L yeast extract, 4.0 g/L magnesium sulfate, 1 g/L urea, 2 g/L calcium chloride, 2 g/L magnesium chloride and 0.25 g/L monopotassium phosphate.

6. The process of claim 5, wherein the carbon source is a sugar.

7. The process of claim 1, wherein one culture medium of the two or more culture medium contains a carbon source, yeast extract and sea salt.

8. The process of claim 7, wherein the carbon source is a sugar.

9. The process of claim 8, wherein the sugar is glucose.

10. The process of claim 1, further comprising culturing the algae in a culture medium containing glucose, yeast extract and sea salt prior to the culturing in the culture medium comprising a carbon source, yeast extract, a magnesium source, and a calcium source.

11. The process of claim 1, wherein the culture medium comprising a carbon source, a yeast extract, a nitrogen source, a phosphate source, a magnesium source, a calcium source, and 4 g/L or less of sodium chloride, wherein the nitrogen and phosphate are in a ratio of 50:1 to 4:1 is supplemented with a fed-batch feed.

12. The process of claim 11, wherein the fed-batch feed comprises urea and monopotassium phosphate.

13. The process of claim 11, wherein the algal biomass is harvested from the culture medium between 12-24 hours after cessation of the fed-batch process.

14. The process of claim 13, wherein the algal biomass is harvested from the culture medium after all of the nutrients have been removed/consumed from the medium.

15. The process of claim 13, wherein the algal biomass is harvested via centrifugation of the culture medium comprising the algal biomass.

16. The process of claim 15, wherein the culture medium is chilled prior to harvesting the algal biomass.

17. The process of claim 16, wherein the culture medium is chilled to between about 5 and 25° C.

18. The process of claim 1, wherein the algae is *Schizochytrium limacinum*.

19. The process of claim 10, wherein the culture medium contains 50 g/L glucose, about 10 g/L yeast extract and about 4 g/L sea salt.

20. The process of claim 1, wherein the culture conditions comprise running the algae culture at 30° C. under airflow and agitation conditions so as to maintain dissolved oxygen at 10%.

21. The process of claim 1, wherein algae are cultured under sterile conditions.

22. The process of claim 1, wherein the culture medium comprising a carbon source, a yeast extract, a nitrogen source, a phosphate source, a magnesium source, a calcium source, and 4 g/L or less of sodium chloride, wherein nitrogen and phosphate are in a ratio of 50:1 to 4:1, has magnesium and calcium in a ratio of 4.5:1 to 1:1.

23. The process of claim 1, wherein the nitrogen source is at least one of urea, peptone, malt extract, meat extract, casamino acid, corn steep liquor, sodium glutamate, ammonium acetate, ammonium sulfate, ammonium chloride, or ammonium nitrate.

* * * * *